United States Patent
Barvian et al.

(10) Patent No.: US 6,982,260 B1
(45) Date of Patent: Jan. 3, 2006

(54) QUINAZOLINES AND THEIR USE FOR INHIBITING CYCLIN-DEPENDENT KINASE ENZYMES

(75) Inventors: Mark Robert Barvian, Ann Arbor, MI (US); Ellen Myra Dobrusin, Ann Arbor, MI (US); James Stanley Kaltenbronn, Ann Arbor, MI (US); Peter L. Toogood, Ann Arbor, MI (US); Roy Thomas Winters, Pinckney, MI (US); Inderjit S. Sidhu, Edmonton (CA); Rajeshwar Singh, Edmonton (CA); Yadagiri Bathini, Alberta (CA); Ronald George Micetich, Sherwood Park (CA)

(73) Assignee: Warner-Lambert Company, Morris Plains, NJ (US)

( * ) Notice: Subject to any disclaimer, the term of this patent is extended or adjusted under 35 U.S.C. 154(b) by 1 day.

(21) Appl. No.: 10/130,843

(22) PCT Filed: Nov. 3, 2000

(86) PCT No.: PCT/US00/30376

§ 371 (c)(1),
(2), (4) Date: May 21, 2002

(87) PCT Pub. No.: WO01/38315

PCT Pub. Date: May 31, 2001

Related U.S. Application Data

(60) Provisional application No. 60/166,840, filed on Nov. 22, 1999.

(51) Int. Cl.
*C07D 239/84* (2006.01)
*C07D 239/78* (2006.01)
*C07D 239/80* (2006.01)
*C07D 403/12* (2006.01)
*A61K 31/517* (2006.01)

(52) U.S. Cl. .............. 514/218; 514/235.5; 514/266.21; 514/266.22; 514/266.4; 544/119; 544/284; 544/292; 540/575

(58) Field of Classification Search ........... 514/266.21, 514/266.22, 266.4, 235.5, 218; 544/284, 544/292, 119; 540/575
See application file for complete search history.

(56) References Cited

U.S. PATENT DOCUMENTS

| 4,734,418 A | 3/1988 | Yokoyama et al. |
| 5,411,963 A * | 5/1995 | Dreikorn et al. ......... 514/266.3 |

FOREIGN PATENT DOCUMENTS

| EP | 0107398 A1 | 9/1983 |
| WO | WO 98/33798 A2 | 8/1998 |
| WO | WO 2001/038315 | 5/2001 |
| WO | WO 2002/022604 | 3/2002 |
| WO | WO 2004/026829 | 4/2002 |
| WO | WO 2002/050065 | 6/2002 |
| WO | WO 2002/057259 | 7/2002 |
| WO | WO 2002/059111 | 8/2002 |
| WO | WO 2002/062789 | 8/2002 |
| WO | WO 2002/066461 | 8/2002 |
| WO | WO 2002/068415 | 9/2002 |
| WO | WO 2004/065378 | 8/2004 |

OTHER PUBLICATIONS

Elslager, E. et. al., "Synthesis and Antimalarial Effects . . . ", J. Med. Chem., 1981, vol. 24, No. 2, pp. 127-140.*
Gran Heinicke, et al. Chemical Abstract, Beillstein Reg. No. 5518665, Feb. 12, 1993.
Arteaga, C., "Blockade Of The Epidermal Growth Factor Receptor Tyrosine Suppresses Tumorigenesis In MMTV/Neu + MMTV/TGF-α Bigenic Mice," *Proceedings of the National Academy of Sciences Of The United States Of America*, 2000, 9609-9614, vol. 97, No. 17.
Bathini, Y., et al., "Synthesis Of Substituted Quinazolines," *Tetrahedron Letters*, 2002, 1-2, vol. 43.
Benson, D., et al., "GenBank," *Nucleic Acids Ressearch*, 2000, 15-18, vol. 28, No. 1.
Dermatakis, A., "ATP-Competitive Inhibitors Of Cyclin-Dependent Kinases," *Frontiers of Biotechnology & Pharmaceuticals*, 2002, 125-156, vol. 3.
Di Gennaro, E., et al., "Critical Role Of Both p27$^{KIP1}$ and p21$^{CIP1/WAF1}$ In The Antiproliferative Effect Of ZD1839 ('Iressa'), An Epidermal Growth Factor Receptor Tyrosine Kinase Inhibitor, In Head And Neck Squamous Carcinoma Cells," *Journal of Cellular Physiology*, 2003, 139-150, vol. 195, No. 1.
Geller, J., et al., "P21$^{Cip1}$ Is A Critical Mediator Of The Cytotoxic Action Of Thymidylate Synthase Inhibitors In Colorectal Carcinoma Cells," *Cancer Research*, 2004, 6296-6303, vol. 64.

(Continued)

*Primary Examiner*—Bruck Kifle
(74) *Attorney, Agent, or Firm*—Bryan C. Zielinski; Wendy L. Hsu

(57) ABSTRACT

This invention provides quinazolines that are useful for treating cell proliferative diseases and disorders, such as cardiovascular diseases, infections, cancers, autoimmune diseases, gout, kidney disease, and neurodegenerative diseases and disorders such as Alzheimer's disease. We have now discovered a group of 2-arylamino-7-(alkyl)oxy-8-alkylquinazolines and 8-alkyl-2-arylamino-quinazoline 2,7-diamines that are potent inhibitors of cyclin-dependent kinases (cdks). The compounds are readily synthesized and can be administered by a variety of routes, including orally, and have sufficient bioavailability. This invention also provides pharmaceutical formulations comprising at least one of the quinazoline compounds together with a pharmaceutically acceptable carrier, diluent, or excipient therefor. The invention further provide useful intermediates generated during the production of the quinazoline compounds.

66 Claims, No Drawings

OTHER PUBLICATIONS

Hennequin, L., et al., "Novel 4-Anilinoquinazolines With C-7 Basic Side Chains: Design And Structure Activity Relationship Of A Series Of Potent, Orally Active, VEGF Receptor Tyrosine Kinase Inhibitors," *Journal of Medicinal Chemistry*, 2002, 1300-1312, vol. 45, No. 6.

Rewcastle, G., et al., "Synthesis of 4-(Phenylamino) Pyrimidine Derivatives As ATP-Competitive Protein Kinase Inhibitors With Potential For Cancer Chemotherapy," Current Organic Chemistry, 2000, 679-706, vol. 4, No. 7.

Sgambato, A., et al., "Targeted Inhibition Of The Epidermal Growth Factor Receptor-Tyrosine Kinase By ZD1839 ('Iressa') Induces Cell-cycle Arrest And Inhibits Proliferation In Prostate Cancer Cells," *Journal Of Cellular Physiology*, 2004, 97-105, vol. 201.

Shewchuk, L., et al., "Binding Mode Of The 4-Anilinoquinazoline Class Of Protein Kinase Inhibitor: X-ray Crystallographic Studies Of 4-Anilinoquinazolines Bound To Cyclin-Dependent Kinase 2 And p38 Kinase," *Journal of Medicinal Chemistry*, 2000, 133-138, vol. 43, No. 1.

Yano, S., et al., "EGFR Tyrosine Kinase Inhibitor Gefitinib (Iressa®)," Japanese Journal of Pharmacology, 2003, 491-497, vol. 122, No. 6.

* cited by examiner

QUINAZOLINES AND THEIR USE FOR INHIBITING CYCLIN-DEPENDENT KINASE ENZYMES

This application is a 371 application of PCT/US00/30376 filed Nov. 3, 2000, which claims the benefit of priority to U.S. provisional application Ser. No. 60/166,840 filed Nov. 22, 1999.

FIELD OF THE INVENTION

This invention relates to quinazolines that inhibit cyclin-dependent kinase enzymes, and as such are useful to treat cell proliferative diseases and disorders, such as cardiovascular diseases (i.e., atherosclerosis, restenosis), and cancer, infections (i.e., viral and fungal), autoimmune diseases, organ transplant rejections (i.e., inflammation), gout, kidney disease, and also neurodegenerative diseases and disorders.

SUMMARY OF THE RELATED ART

Cyclin-dependent kinases and related serine/threonine protein kinases are important cellular enzymes that perform essential functions in regulating cell division and proliferation. The cyclin-dependent kinase catalytic units, of which 9 have now been described, are activated by regulatory subunits known as cyclins. At least 16 mammalian cyclins have been identified (Johnson D. G. and Walker C. L., *Annu. Rev. Pharmcol. Toxicol.* 1999;39:295–312). Cyclin B/Cdk1, Cyclin A/Cdk2, Cyclin E/Cdk2, Cyclin D/Cdk4, Cyclin D/Cdk6, and probably other heterodimers including Cdk3 and Cdk7 are important regulators of cell cycle progression. Additional functions of Cyclin/Cdk heterodimers include regulation of transcription, DNA repair, differentiation and apoptosis (Morgan D. O., *Annu. Rev. Cell. Dev. Biol.* 1997; 1361–191).

Increased activity or temporally abnormal activation of cyclin-dependent kinases has been shown to result in the development of human tumors (Sherr C. J., *Science* 1996; 274:1672–1677). Indeed, human tumor development is commonly associated with alterations in either the Cdk proteins themselves or their regulators (Cordon-Cardo C., *Am. J. Pathol.* 1995;147:545–560; Karp J. E. and Broder S., *Nat. Med.* 1995;1:309–320; Hall M. et al., *Adv. Cancer Res.* 196;68:67–108). These and other observations have prompted an intensive search for small molecule Cdk inhibitors. Strong validation for this approach is provided by studies of naturally occurring protein inhibitors of Cdks (Kamb A., *Curr. Top. Microbiol. Immunol.* 1998;227:139–148). Introduction of p16 into lung cancer cell lines blocked entry into S phase and caused growth inhibition (Jin X. et al., *Cancer Res.* 1995;55:3250–3253; Chintaia S. K. et al., *Oncogene* 1997;15:2049–2057). Other studies demonstrated a similar effect for p27 (Craig C. et al., *Oncogene* 1997;14:2283–2289). Ectopic expression of the Cdk inhibitors p21 or p27 in U937 human leukemia cells resulted in growth arrest and cellular differentiation (Liu et al., *Genes Dev.*, 1996;10:142–153). Markers of differentiation also were observed in the non-small lung cancer cell line NCI-H358 following expression of antisense Cdk2. Expression of antisense cyclin D1 in human esophageal cancer cells resulted in growth inhibition (Zhou P. et al., *Oncogene*, 1995;11:571–580).

Further support for targeting Cdk2 with therapeutic agents is found in the work of Chen et al., *Proc. Natl. Acad. Sci.* (USA) 1999;95:4325–4329, who demonstrated selective killing of transformed U2OS cells containing deregulated E2F using peptide inhibitors of Cyclin A/Cdk2. Untransformed cell lines were unaffected by these inhibitors. Thus, Cdk inhibitors potentially could demonstrate efficacy in vivo with a useful margin of safety.

In addition to treating cancer, Cdk inhibitors also may have potential applications in the treatment of cardiovascular disorders such as restenosis and atherosclerosis. Vascular smooth muscle proliferation and intimal hyperplasia following balloon angioplasty are inhibited by over-expression of the cyclin-dependent kinase inhibitor protein p21 (Chang M. W. et al., *J. Clin. Invest.*, 1995;96:2260; Yan Z-Y. et al., *Proc. Natl. Acad. Sci.* (USA) 1996;93:9905. Moreover, intraluminal exposure of a denuded rat carotid artery to the purine Cdk2 inhibitor CVT-313 (Ki=95 nM) resulted in greater than 80% inhibition of neointima formation (Brooks E. E. et al., *J. Biol. Chem.* 1997:29207–29211). Taken together, these observations support the use of small molecule inhibitors of cell cycle progression in the treatment of vascular disorders that are due to aberrant cell proliferation.

The neuronal Cdc2-like kinase, known as Cdk5, together with its brain specific activator protein p35/p25, phosphorylates the neuron-specific microtubule-associated protein tau (Lew J. and Wang J. H., *Trends Biochem. Sci.* 1995;20: 33–37). Aberrant expression of Cdk5 is proposed to contribute to the neurodegenerative disorder Multiple System Atrophy (Nakamura S. et al., *J. Neuropathol. Exp. Neurol.* 1998;57:690) and tau hyperphosphorylation has long been associated with the pathogenesis of Alzheimer's Disease (AD) (Spillantini M. G. and Giedert M., *Trends Neurosci.* 1998;21:428–433). In addition to amyloid plaques, neurofibrillary tangles (NFTs) are a primary marker for AD. The major component of NFTs are paired helical filament (PHF)-tau, which is a filamentous aggregate of hyperphosphorylated tau. The "NFT load" in the brains of Alzheimer's Disease (AD) patients is strongly correlated with severity of the disease. This correlation is stronger than that seen for Aβ-rich amyloid plaques. Abnormal activation of protein kinases (cyclin-dependent kinase 5 (Cdk5), glycogen synthase kinase-3β (GSK-3β)), and protein phosphatases (type 2A and 2B), has been implicated in tau hyperphosphorylation and pathological activation of Cdk5 is likely a major contributor to PHF-tau.

Cdk5 is an important therapeutic target because its activator protein p35 is specifically localized in central and peripheral neurons (Tsai J.-H. et al., *Nature* 1984;371: 419–423). Indeed the abnormal deposition of amyloid beta peptide (from the APP gene) and hyperphosphorylated tau may be combined factors that lead to early onset AD (Mandelkow E.-M. and Mandelkow E., *Trends Cell Biol.* 1998;8:425–427). There is growing evidence that abnormally processed tau also is associated with other CNS diseases. Recently, mutations in the tau gene on chromosome 14 have been linked to fronto-temporal dementia with Parkinsonism (FTDP-17) and progressive supernuclear palsy (PSP) (Spillantini M. G. and Giedert M., *Trends Neurosci.* 1998;21:428–433).

Further evidence supporting the role of Cdk5 in tauopathy and Alzheimer's disease include the following observations. (1) Increased Cdk5 activity has been found in AD brains (Pei J. J. et al., *Brain Res.* 1998;797:267–77; Lee K. Y. et al., *Neurosci Res.* 1999;34:21–9). (2) PHF-Tau found in AD brains has 8 phosphorylation sites that overlap with the sites of cdk5 phosphorylation (Paudel H. K. et al., *J. Biol. Chem.* 1993;268:23512–23518; Baumann K. et al., *FEBS Lett.* 1993;336:417–424). (3) Synergy among the different tau protein kinases eg, Cdk5-phosphorylated tau is more readily phosphorylated by GSK3 (Sengupta A., et al., *Mol. Cell. Biochem.* 1997; 167:99–105).

Other diseases in which Cdk inhibitors could find application include those caused by a variety of infectious agents, including DNA and RNA viruses. For example, cyclin-dependent kinases are required for viral replication following infection by herpes simplex virus (HSV) (Schang L. M. et al., *J. Virol.* 1998;72:5626). HSV replication was inhibited by the cyclin-dependent kinase inhibitors roscovitine and olomoucine but not by a cell cycle inhibitor that does not inhibit cyclin-dependent kinase activity. Inactivation of the Cdk inhibitor protein p16 by the viral protein Tax, and inactivation of p27 by viral E1A, have both been demonstrated to overcome cell cycle suppression and to promote cell immortalization and the transformed phenotype (Mal A. et al., *Nature* 1996;380:262–265; Suzuki T. et al., *EMBO J.* 1996;15:1607–1614; Parker G. A. et al., *Oncogene* 1996; 13:2541–2549). Cdk2 also has been implicated in the progression of cytomegalovirus infections (Bresnahan W. A. et al., *Virology* 1997;231:239–247; Albrecht T. et al., WO 98/39007). Fungal infections may be expected to be susceptible to Cdk inhibitors on the basis of the known essential roles of Cdk homologs in yeast.

It is further possible that various autoimmune disorders may succumb to treatment with selective Cdk inhibitors. The chronic inflammatory disease rheumatoid arthritis is characterized by synovial tissue hyperplasia; inhibition of synovial tissue proliferation should minimize inflammation and prevent joint destruction. Consistent with this idea, expression of the Cdk inhibitor protein p16 in synovial fibroblasts led to growth inhibition (Taniguchi K. et al., *Nat. Med.* 1999;5:760–767). Similarly, in a rat model of arthritis, joint swelling was substantially inhibited by treatment with a p16 expressing adenovirus. By extension, Cdk inhibitors may be effective against other disorders of cell proliferation including psoriasis (characterized by keratinocyte hyperproliferation) and possibly lupus.

Distinct from gene therapy approaches, many research groups are pursuing small molecule inhibitors of cyclin dependent kinases. Small molecule inhibitors of Cdks that have been published to date include purines such as olomoucine (Vesely et al., *Eur. J. Biochem.* 1994;224:771–786) and roscovitine (Meijer L. et al., *Eur. J. Biochem.* 1997;243: 527–536), butyrolactone, staurosporine and UCN-01, suramin, 9-hydroxyellipticine, and several flavonoids including flavopiridol (Garrett M. D. and Fattaey A., *Curr. Opin. Genes & Develop.* 1999;9:104–111; Walker D. H., *Curr. Top. Microbio. Immunol.* 1998:148–165; Meijer L., *Meths. In Enzymol.* 1997;223:113–128). Of these inhibitors, most information is available for flavopiridol.

Flavopiridol is currently in phase II clinical trials for the treatment of metastatic renal cell carcinoma. It is a relatively nonspecific inhibitor of Cdks and produces cell cycle blocks at G1 and G2. Nonetheless, it is a potent inhibitor of several breast and lung cancer cell lines (Sedlacek H. H. et al., *Int. J. Oncol.* 1996:1143–1168; Kaur et al., *J. Natl. Cancer Inst.* 1992;84:1736–1740; Bible K. C. and Kaufman S. H., *Cancer Res.* 1996;56:4856–4861) and displays growth inhibitory activity against tumors in vivo (Patel V. et al., *J. Clin. Invest.* 1998;102:1674–1681; Drees M. et al., *Clin. Cancer Res.* 1997;3:273–279; Wright J. et al., *Oncology* 1998;12: 1018, 1023–1014; Senderowicz A. M. et al., *J. Clin. Oncol.* 1998;16 2988–2999). Flavopiridol analogs have been described by Mitotix (International patent application WO 97/16447; U.S. Pat. No. 5,733,920) as well as by Bristol-Myers Squibb (WO 97/42949).

The purine class of Cdk inhibitors have been extensively studied in vitro, generally displaying most potency against Cdk1, Cdk2 and Cdk5. Analogs of olomoucine have been synthesized by Meijer and coworkers (Legraverand M. et al., *Bioor. Med. Chem.* 1999;7:1281–1293 and references therein), Schultz and coworkers (Chang Y-T. et al., *Chem. & Biol.* 1999;6:361–375), Griffin et al. (International patent application WO 99/02162) and Mackman et al., (U.S. Pat. No. 5,866,702; WO 98/05335), among others. One of these compounds has been shown to inhibit neointimal formation in an animal model of restenosis (see above).

Other classes of small molecule Cdk inhibitors described in the patent literature include aminothiazoles developed independently by Agouron (WO 99/21845) and by Bristol-Myers Squibb (WO 99/24416); indolinones, that have been developed by Sugen (WO 98/50356) and by Glaxo (WO 99/24416); benzothiadiazines (WO 98/49146); peptides (WO 97/11174); pyrazolo-[3,4-b]pyridines (WO 99/30710); and phenylaminopyrimidines (Novartis, unpublished results). Several of these structural classes of protein kinase inhibitors have been reviewed by McMahon et al., *Curr. Opin. Drug, Discovery & Develop.* 1998/1:131–146). Very little in vitro data and no clinical data are available for any of these compounds, and there is still a need for more potent and selective Cdk inhibitors with good pharmacokinetic properties that can be employed not just as in vitro tools but also in vivo.

We have previously described a class of pyrido[2,3d] pyrimidines that display selectivity for Cdks versus other protein kinases (WO 98/33798). These compounds are distinct from the 6-aryl-pyrido[2,3d]pyrimidines (WO 96/15128; WO 96/34867) which display the opposite selectivity, preferring tyrosine kinases over cyclin-dependent kinases. Moreover, they represent a new structural class when compared to either the pyrimidines and 3,4-dihydropyrimidines of International Patent application, PCT/US99/10187, filed May 10, 1999, or the naphthyridones described in international patent application WO 99/09030.

Despite the progress that has been made, the search continues for small molecular weight compounds that are orally bioavailable and useful for treating a wide variety of cell proliferative diseases and disorders, cancer, infections, autoimmune diseases, gout, kidney disease, and neurodegenerative diseases and disorders.

SUMMARY OF THE INVENTION

This invention provides quinazolines that are useful for treating cell proliferative disorders, such as vascular smooth muscle proliferation associated with atherosclerosis, post-surgical vascular stenosis and restenosis, and endometriosis.

This invention also provides quinazolines that are useful for treating infections, including viral infections such as DNA viruses like herpes and RNA viruses like HIV, and fungal infections.

This invention further provides quinazolines that are useful for treating autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease.

This invention further provides quinazolines that are useful for treating and neurodegenerative disorders such as Alzheimer's disease.

This invention further provides quinazolines that are useful for treating cancer.

This invention further provides quinazolines that are useful for treating gout.

This invention further provides quinazolines that are useful for treating kidney disease, such as polycystic kidney disease.

The above-identified methods of treatment are preferably carried out by administering a therapeutically effective amount of a compound of Formulas I and/or II (set forth below) to a subject in need of treatment. It has been discovered that a group of 2-arylamino-7-(alkyl)oxy-8-alkylquinazolines and 8-alkyl-2-arylamino-quinazoline 2,7-diamines are potent inhibitors of cyclin-dependent kinases (cdks). The compounds are readily synthesized and can be administered by a variety of routes, including orally and parenterally, and have little or no toxicity. The compounds of the invention are members of the class of compounds of Formulas I and II, which will be described further below.

This invention also provides pharmaceutical formulations comprising a compound of Formulas I or II together with a pharmaceutically acceptable carrier, diluent, or excipient therefor.

Compounds within the scope of the present invention are inhibitors of the cyclin-dependent kinases such as cdk1, cdk2, cdk4, and cdk5.

DETAILED DESCRIPTION OF THE INVENTION

A new class of compounds have been discovered that are potent inhibitors of cyclin-dependent kinases (cdks) and are useful agents for treating subjects suffering from diseases caused by abnormal cell proliferation. Compounds within the scope of the present invention are inhibitors of the cyclin-dependent kinases such as cdk1, cdk2, cdk4, and cdk5. As inhibitors of cyclin-dependent kinases, the compounds of the instant invention are useful in controlling proliferative diseases and disorders, cancer, infections, autoimmune diseases, gout, kidney disease, and neurodegenerative diseases and disorders.

The compounds of the invention comprise those of Formula I:

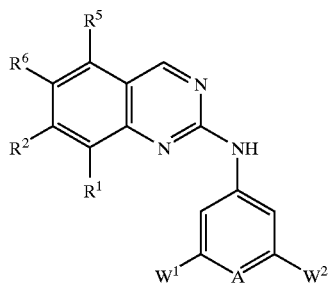

wherein,
$R^1$ is hydrogen, alkyl, alkyl substituted with at least one of amine, halogen, hydroxy, or alkoxy, cycloalkyl, or heterocycloalkyl;
$R^2$ is OH, alkyloxy, aryloxy, or $NR^3R^4$;
A is N, or $CW^3$;
$R^3$ and $R^4$ are independently hydrogen, alkyl, alkenyl, alkynyl, $(CH_2)_nAr$, cycloalkyl, heterocycloalkyl, or heteroaryl, or $R^3$ and $R^4$ together with the nitrogen to which they are attached optionally may form a ring having 3 to 7 carbon atoms and said ring optionally contains 1, 2 or 3 heteroatoms selected from the group consisting of nitrogen, substituted nitrogen, oxygen and sulfur including S(O) and S(O)$_2$. Said ring also may be additionally substituted with up to 3 groups selected from alkyl, haloalkyl, $NR^8C(O)R^9$, $C(O)OR^8$, $C(O)R^8$, $C(O)NR^8R^9$, $NR^8R^9$, $NR^8SO_2R^9$, $OR^8$, $SO_2NR^3R^4$, or $SR^8$;

$W^1$ and $W^2$ are independently selected from $NR^3R^4$, $N(O)R^3R^4$, $NR^3R^4X$, $OR^3$, $SR^3$, hydrogen, halogen, haloalkyl, $COR^3$, $CO_2R^3$, $CONR^3R^4$, $S(O)R^3$, $SO_2R^3$, $SO_2NR^3R^4$, $SO_3R^3$, $P(O)(OR^3)_2$, aldehyde, nitrile, nitro, alkyl, $T(CH_2)_mQR^8$, $C(O)T(CH_2)_mQR^8$, or $T(CH^2)_mCO_2R^8$ where m is 1–6, T is O, S, $NR^3$, $N(O)R^3_9$, $NR^3R^4X$, or $CR^3R^4$, and Q is O, S, $NR^9$, $N(O)R^9$ or $NR^9R^{10}X$, or $NR^9C(O)T(CH_2)_mQR^9$;

$R^5$ is hydrogen, or alkyl;
$R^6$ is hydrogen, alkyl, halogen, haloalkyl, alkynyl, alkenyl, $COR^3$, $CO_2R^3$, $CONR^3R^4$, $SO_2NR^3R^4$, $SO_2R^3$, $SO_3R^3$, $P(O)(OR^3)_2$, aldehyde, nitrile, nitro, $OR^3$, or $NR^3R^4$ $W^3$ is $NR^3R^4$, $N(O)R^3R^4$, $NR^3R^4R^8X$, OH, $OR^3$, SH, $SR^3$, halogen, $COR^3$, $CO_2R^3$, $CONR^3R^4$, $S(O)R^3$, $SO_2R^3$, $SO_2NR^3R^4$, $SO_3R^3$, $(CH_2)_nP(O)(OR^3)_2$, $NR^3SO_2R^4$, aldehyde, nitrile, nitro, alkyl, $T(CH_2)_mQR^8$, $C(O)T(CH_2)_mQR^8$, $NR^8C(O)T(CH_2)_mQR^{11}$, or $T(CH^2)_mCO_2R^3$ where m and n are independently 1–6, T is O, S, $NR^3$, $N(O)R^3$, $NR^3R^4W$, or $CR^3R^4$, and Q is O, S, $NR^9$, $N(O)R^9$ or $NR^9R^{10}X$;

$R^8$, $R^9$, $R^{10}$ and $R^{11}$ are hydrogen, alkyl, or aryl;
X is halogen;
or a pharmaceutically acceptable salt, ester, amide or pro-drug thereof.

The compounds of the invention further comprise those of formula II:

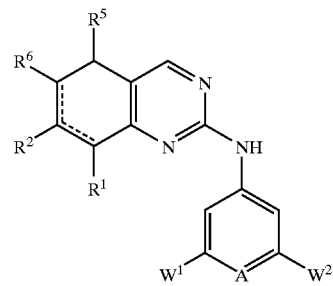

wherein,
the dotted line represents a bond at the $C_5$–$C_6$, $C_6$–$C_7$, or $C_7$–$C_8$ position,
$R^1$ is hydrogen, alkyl, alkyl substituted with at least one amine, halogen, hydroxy, or alkoxy, cycloalkyl, or heterocycloalkyl;
$R^2$ is OH, alkyloxy, aryloxy, or $NR^3R^4$;
A is N, or $CW^3$;
$R^3$ and $R^4$ are independently hydrogen, alkyl, alkenyl, alkynyl, $(CH_2)_nAr$, cycloalkyl, heterocycloalkyl, or heteroaryl, or $R^3$ and $R^4$ together with the nitrogen to which they are attached optionally may form a ring having 3 to 7 carbon atoms and said ring optionally contains 1, 2 or 3 heteroatoms selected from the group consisting of nitrogen, substituted nitrogen, oxygen and sulfur including S(O) and S(O)$_2$. Said ring also may be additionally substituted with up to 3 groups selected from alkyl, haloalkyl, $NR^8C(O)R^9$, $C(O)OR^8$, $C(O)R^8$, $C(O)NR^8R^9$, $NR^8R^9$, $NR^8SO_2R^9$, $OR^8$, $SO_2NR^3R^4$, or $SR^8$;

$W^1$ and $W^2$ are independently selected from $NR^3R^4$, $N(O)R^3R^4$, $NR^3R^4X$, $OR^3$, $SR^3$, hydrogen, halogen, haloalkyl, $COR^3$, $CO_2R^3$, $CONR^3R^4$, $S(O)R^3$, $SO_2R^3$, $SO_2NR^3R^4$, $SO_3R^3$, $P(O)(OR^3)_2$, aldehyde, nitrile, nitro, alkyl, $T(CH_2)_mQR^8$, $C(O)T(CH_2)_mQR^8$, or $T(CH_2)_mCO_2R^8$ where m is 1–6, T is O, S, $NR^3$, $N(O)R^3$, $NR^3R^4X$, or $CR^3R^4$, and Q is O, S, $NR^9$, $N(O)R^9$ or $NR^9R^{10}X$, or $NR^9C(O)T(CH_2)_mQR^9$;

$R^5$ is hydrogen, or alkyl;

$R^6$ is hydrogen, alkyl, halogen, haloalkyl, alkynyl, alkenyl, $COR^3$, $CO_2R^3$, $CONR^3R^4$, $SO_2NR^3R^4$, $SO_2R^3$, $SO_3R^3$, $P(O)(OR^3)_2$, aldehyde, nitrile, nitro, $OR^3$, or $NR^3R^4$ $W^3$ is $NR^3R^4$, $N(O)R^3R^4$, $NR^3R^4R^8X$, OH, $OR^3$, SH, $SR^3$, halo, $COR^3$, $CO_2R^3$, $CONR^3R^4$, $S(O)R^3$, $SO_2R^3$, $SO_2NR^3R^4$, $SO_3R^3$, $(CH_2)_nP(O)(OR^3)_2$, $NR^3SO_2R^4$, aldehyde, nitrile, nitro, alkyl, $T(CH_2)_mQR^8$, $C(O)T(CH_2)_mQR^8$, $NR^8C(O)T(CH_2)_mQR^{11}$, or $T(CH_2)_mCO_2R^3$ where n and m independently are 1–6, T is O, S, $NR^3$, $N(O)R^3$, $NR^3R^4W$, or $CR^3R^4$; and Q is O, S, $NR^9$, $N(O)R^9$ or $NR^9R^{10}X$;

$R^8$, $R^9$, $R^{10}$ and $R^{11}$ are hydrogen, alkyl, or aryl;

X is a halogen;

or a pharmaceutically acceptable salt, ester, amide or pro-drug thereof.

Preferred examples of $W^3$ include piperidine; piperidine substituted with up to 2 groups consisting of alkyl, haloalkyl, $OR^9$, $(CH_2)_nOR^9$, $CO_2R^9$, $CONR^9R^{10}$, $NR^9R^{10}$; 3-aminopyrrolidine, 3-acylaminopyrrolidine; 3-alkylaminopyrrolidine, 3-aminoalkylpyrrolidine; pyrrolidine substituted with up to 3 groups selected from alkyl, haloalkyl, $NR^8C(O)R^9$, $C(O)NR^8R^9$, $NR^8R^9$, $OR^8$; piperazine; N-acylpiperazine; N-aminoacylpiperazine; piperazine substituted with up to five groups selected from alkyl, haloalkyl, $OR^8$, $(CH_2)_nOR^8$, $CO_2R^8$, $NR^8C(O)R^9$, $C(O)NR^8R^9$, $NR^8R^9$, $SO_2R$, $SO_2NR^8R^9$; piperazine substituted on nitrogen with a group selected from alkyl, haloalkyl, $OR^8$, $(CH_2)_nOR^8$, $CO_2R^8$, $CONR^8R^9$, $NR^8R^9$, $SO_2R$, $SO_2NR^8R^9$; homopiperazine; N-acylhomopiperazine; N-alkylhomopiperazine; N-haloalkylhomopiperazine; tetrahydro-1,4-pyrimidone. Especially preferred groups include N-acetylpiperazine, 3,5-dimethylpiperazine, 3,3,4-trimethylpiperazinyl, N-methylpiperazine, homopiperazine, N-acetylhomopiperazine, N-tert-butylacetylpiperazine, N-pivaloylpiperazine, N-leucylpiperazine, N-isoleucylpiperazine; N-valylpiperazine, N-prolylpiperazine, N-alanylpiperazine, and N-glycylpiperazine.

A preferred group of compounds of Formulas I and II have the above formulas wherein $R^1$ is alkyl.

Another preferred group of compounds of Formulas I and II have the above formulas wherein $R^1$ is isopropyl.

Another preferred group of compounds of Formulas I and II have the above formulas wherein $R^1$ is cycloalkyl.

Another preferred group of compounds of Formulas I and II have the above formulas wherein $R^1$ is cyclopentyl.

Another preferred group of compounds of Formulas I and II have the above formulas wherein $R^2$ is hydroxy.

Another preferred group of compounds of Formulas I and II have the above formulas wherein $R^2$ is alkyloxy.

Another preferred group of compounds of Formulas I and II have the above formulas wherein $R^2$ is methoxy.

Another preferred group of compounds of Formulas I and II have the above formulas wherein $R^2$ is $NR^3R^4$.

Another preferred group of compounds of Formulas I and II have the above formulas wherein A is $CW^3$.

Another preferred group of compounds of Formulas I and II have the above formulas wherein $W^3$ is piperidine.

Another preferred group of compounds of Formulas I and II have the above formulas wherein $W^3$ is substituted piperidine.

Another preferred group of compounds of Formulas I and II have the above formulas wherein $W^3$ is pyrolidine.

Another preferred group of compounds of Formulas I and II have the above formulas wherein $W^3$ is substituted pyrolidine.

Another preferred group of compounds of Formulas I and II have the above formulas wherein $W^3$ is piperazine.

Another preferred group of compounds of Formulas I and II have the above formulas wherein $W^3$ is substituted piperazine.

Another preferred group of compounds of Formulas I and II have the above formulas wherein $W^3$ is hydrogen.

Another preferred group of compounds of Formulas I and II have the above formulas wherein $W^2$ and $W^3$ are hydrogen.

Another preferred group of compounds of Formulas I and II have the above formulas wherein $R^5$ is hydrogen.

Another preferred group of compounds of Formulas I and II have the above formulas wherein $R^5$ is alkyl.

Another preferred group of compounds of Formulas I and II have the above formulas wherein $R^6$ is hydrogen.

Another preferred group of compounds of Formulas I and II have the above formulas wherein $R^6$ is alkyl.

Another preferred group of compounds of Formulas I and II have the above formulas wherein $W^1$, $W^2$, and $W^3$ are hydrogen.

Another preferred group of compounds of Formulas I and II have the above formulas wherein $R^5$ and $R^6$ are hydrogen.

A particularly preferred group of compounds of Formulas I and II have the above formulas wherein $W^1$, $W^2$, and $W^3$ are hydrogen, and $R^1$ is alkyl.

Another particularly preferred group of compounds of Formulas I and II have the above formulas wherein $W^1$, $W^2$, and $W^3$ are hydrogen, and $R^1$ is cycloalkyl.

A further particularly preferred group of compounds of Formulas I and II have the above formulas wherein $W^3$ is piperidine or substituted piperidine, and $R^1$ is alkyl or cycloalkyl.

A further particularly preferred group of compounds of Formulas I and II have the above formulas wherein $W^3$ is pyrrolidine or substituted pyrrolidine, and $R^1$ is alkyl or cycloalkyl.

A further particularly preferred group of compounds of Formulas I and II have the above formulas wherein $W^3$ is piperazine or substituted piperazine, and $R^1$ is alkyl or cycloalkyl.

A further particularly preferred group of compounds of Formulas I and II have the above formulas wherein $W^3$ is piperidine or substituted piperidine, $R^2$ is alkyloxy, and $R^1$ is alkyl or cycloalkyl.

A further particularly preferred group of compounds of Formulas I and II have the above formulas wherein $W^3$ is pyrrolidine or substituted pyrrolidine, $R^2$ is alkyloxy, and $R^1$ is alkyl or cycloalkyl.

A further particularly preferred group of compounds of Formulas I and II have the above formulas wherein $W^3$ is piperazine or substituted piperazine, $R^2$ is alkyloxy, and $R^1$ is alkyl or cycloalkyl.

The following compounds illustrate specific embodiments provided by the present invention, and the compound listed below are among the preferred embodiments:

(8-Isopropyl-7-methoxy-quinazolin-2-yl)-phenyl-amine;
(8-Cyclopentyl-7-methoxy-quinazolin-2-yl)-phenyl-amine;
(8-Isopropyl-7-methoxy-quinazolin-2-yl)-(4-piperidin-1-yl-phenyl)-amine;
(8-Isopropyl-7-methoxy-quinazolin-2-yl)-(4-pyrrolidin-1-yl-phenyl)-amine;
(8-Cyclopentyl-7-methoxy-quinazolin-2-yl)-(4-piperidin-1-yl-phenyl)-amine;
(8-Cyclopentyl-7-methoxy-quinazolin-2-yl)-(4-pyrrolidin-1-yl-phenyl)-amine;
8-Isopropyl-2-phenylamino-quinazolin-7-ol;
4-[4-(8-Isopropyl-7-methoxy-quinazolin-2-ylamino)-phenyl]-piperazine-1-carboxylic acid tert-butyl ester;
4-[4-(8-Cyclopentyl-7-methoxy-quinazolin-2-ylamino)-phenyl]-piperazine-1-carboxylic acid tert-butyl ester;
(8-Cyclopentyl-7-methoxy-quinazolin-2-yl)-(4-piperazin-1-yl-phenyl)-amine;
8-Cyclopentyl-2-(4-piperazin-1-yl-phenylamino)-quinazolin-7-ol;
2-Amino-1-{4-[4-(8-cyclopentyl-7-methoxy-quinazolin-2-ylamino)-phenyl]-piperazin-1-yl}-ethanone;
8-Isopropyl-2-(4-piperazin-1-yl-phenylamino)-quinazolin-7-ol;
(8-Isopropyl-7-methoxy-quinazolin-2-yl)-(4-piperazin-1-yl-phenyl)-amine;
2-Amino-1-{4-[4-(8-cyclopentyl-7-hydroxy-quinazolin-2-ylamino)-phenyl]-piperazin-1-yl}-ethanone;
2-Amino-1-{4-[4-(8-isopropyl-7-methoxy-quinazolin-2-ylamino)-phenyl]-piperazin-1-yl}-ethanone;
2-Amino-1-{4-[4-(7-hydroxy-8-isopropyl-quinazolin-2-ylamino)-phenyl]-piperazin-1-yl}-ethanone;
2-Amino-1-{4-[4-(8-cyclopentyl-7-methoxy-quinazolin-2-ylamino)-phenyl] -piperazin-1-yl}-4-methyl-pentan-1-one;
2-Amino-1-{4-[4-(8-cyclopentyl-7-hydroxy-quinazolin-2-ylamino)-phenyl] -piperazin-1-yl}-4-methyl-pentan-1-one;
2-Amino-1-{4-[4-(8-isopropyl-7-methoxy-quinazolin-2-ylamino)-phenyl] -piperazin-1-yl}-4-methyl-pentan-1-one;
2-Amino-1-{4-[4-(7-hydroxy-8-isopropyl-quinazolin-2-ylamino)-phenyl] -piperazin-1-yl}-4-methyl-pentan-1-one;
N-(4-{4-[4-(8-cyclopentyl-7-methoxy-quinazolin-2-ylamino)-phenyl] -piperazin-1-yl}-4-oxo-butyl)-acetamide;
N-(4-{4-[4-(8-Cyclopentyl-7-hydroxy-quinazolin-2-ylamino)-phenyl] -piperazin-1-yl}-4-oxo-butyl)-acetamide;
N-(4-{4-[4-(8-isopropyl-7-methoxy-quinazolin-2-ylamino)-phenyl] -piperazin-1-yl}-4-oxo-butyl)-acetamide;
N-(4-{4-[4-(7-Hydroxy-8-isopropyl-quinazolin-2-ylamino)-phenyl] -piperazin-1-yl}-4-oxo-butyl)-acetamide;
8-Isopropyl-2-(pyridin-4-ylamino)-quinazolin-7-ol;
(8-Isopropyl-7-methoxy-quinazolin-2-yl)-pyridin-4-yl-amine;
(8-cyclopentyl-7-methoxy-quinazolin-2-yl)-pyridin-4-yl-amine;
8-cyclopentyl-2-(pyridin-4-ylamino)-quinazolin-7-ol;
(8-Cyclopentyl-7-methoxy-quinazolin-2-yl)-[4-(5-methyl-hexahydro-pyrrolo[ 3,4-c]pyrrol-2-yl)-phenyl]-amine;
8-Cyclopentyl-2-[4-(5-methyl-hexahydro-pyrrolo[3,4-c]pyrrol-2-yl)-phenylamino] -quinazolin-7-ol;
(8-Isopropyl-7-methoxy-quinazolin-2-yl)-[4-(5-methyl-hexahydro-pyrrolo[ 3,4-c]pyrrol-2-yl)-phenyl]-amine;
8-Isopropyl-2-[4-(5-methyl-hexahydro-pyrrolo[3,4-c]pyrrol-2-yl)-phenylamino] -quinazolin-7-ol;
[4-(3-Amino-pyrrolidin-1-yl)-phenyl]-(8-cyclopentyl-7-methoxy-quinazolin-2-yl)-amine;
2-[4-(3-Amino-pyrrolidin-1-yl)-phenylamino]-8-cyclopentyl-quinazolin-7-ol;
[4-(3-Amino-pyrrolidin-1-yl)-phenyl]-(8-isopropyl-7-methoxy-quinazolin-2-yl)-amine;
2-[4-(3-Amino-pyrrolidin-1-yl)-phenylamino]-8-isopropyl-quinazolin-7-ol;
(4-Fluoro-3-trifluoromethyl-phenyl)-(8-isopropyl-7-methoxy-quinazolin-2-yl)-amine;
2-(4-Fluoro-3-trifluoromethyl-phenylamino)-8-isopropyl-quinazolin-7-ol;
(4-Fluoro-3-trifluoromethyl-phenyl)-(8-cyclopentyl-7-methoxy-quinazolin-2-yl)-amine;
2-(4-Fluoro-3-trifluoromethyl-phenylamino)-8-cyclopentyl-quinazolin-7-ol;
N-{1-[4-(8-Cyclopentyl-7-methoxy-quinazolin-2-ylamino)-phenyl] -pyrrolidin-3-yl}-acetamide;
N-{1-[4-(8-Cyclopentyl-7-hydroxy-quinazolin-2-ylamino)-phenyl] -pyrrolidin-3-yl}-acetamide;
N-{1-[4-(8-Isopropyl-7-methoxy-quinazolin-2-ylamino)-phenyl] -pyrrolidin-3-yl}-acetamide;
N-{1-[4-(8-Isopropyl-7-hydroxy-quinazolin-2-ylamino)-phenyl] -pyrrolidin-3-yl}-acetamide;
1-{4-[4-(8-Isopropyl-7-methoxy-quinazolin-2-ylamino)-phenyl]-piperazin-1-yl}-ethanone;
1-{4-[4-(7-Hydroxy-8-isopropyl-quinazolin-2-ylamino)-phenyl]-piperazin-1-yl}-ethanone;
{4-[4-(8-Cyclopentyl-7-methoxy-quinazolin-2-ylamino)-phenyl] -piperazin-1-yl}-pyrrolidin-2-yl-methanone;
{4-[4-(8-Cyclopentyl-7-Hydroxy-quinazolin-2-ylamino)-phenyl] -piperazin-1-yl}-pyrrolidin-2-yl-methanone;
1-{4-[4-(8-Cyclopentyl-7-methoxy-quinazolin-2-ylamino)-phenyl] -piperazin-1-yl}-ethanone;
1-{4-[4-(8-Cyclopentyl-7-hydroxy-quinazolin-2-ylamino)-phenyl] -piperazin-1-yl}-ethanone;
{4-[4-(8-Isopropyl-7-methoxy-quinazolin-2-ylamino)-phenyl]-piperazin-1-yl}-pyrrolidin-2-yl-methanone;
{4-[4-(7-Hydroxy-8-isopropyl-quinazolin-2-ylamino)-phenyl]-piperazin-1-yl}-pyrrolidin-2-yl-methanone;
2-Amino-1-{4-[4-(8-isopropyl-7-methoxy-quinazolin-2-ylamino)-phenyl] -piperazin-1-yl}-propan-1-one;
2-Amino-1-{4-[4-(7-hydroxy-8-isopropyl-quinazolin-2-ylamino)-phenyl] -piperazin-1-yl}-propan-1-one;
2-Amino-1-{4-[4-(8-cyclopentyl-7-methoxy-quinazolin-2-ylamino)-phenyl] -piperazin-1-yl}-propan-1-one;
2-Amino-1-{4-[4-(8-cyclopentyl-7-hydroxy-quinazolin-2-ylamino)-phenyl] -piperazin-1-yl}-propan-1-one;
1-{4-[4-(8-Cyclopentyl-7-methoxy-quinazolin-2-ylamino)-phenyl] -piperazin-1-yl}-propan-1-one;
1-{4-[4-(8-Cyclopentyl-7-hydroxy-quinazolin-2-ylamino)-phenyl] -piperazin-1-yl}-propan-1-one;
1-{4-[4-(8-Isopropyl-7-methoxy-quinazolin-2-ylamino)-phenyl]-piperazin-1-yl}-propan-1-one;
1-{4-[4-(7-Hydroxy-8-isopropyl-quinazolin-2-ylamino)-phenyl]-piperazin-1-yl}-propan-1-one;
8-Isopropyl-2-phenylamino-5,6-dihydro-quinazolin-7-ol;
(8-Isopropyl-7-methoxy-5,6-dihydro-quinazolin-2-yl)-phenyl-amine;
8-Isopropyl-2-phenylamino-5,8-dihydro-quinazolin-7-ol;
(8-Isopropyl-7-methoxy-5,8-dihydro-quinazolin-2-yl)-phenyl-amine;

8-Cyclopentyl-2-phenylamino-5,6-dihydro-quinazolin-7-ol;
(8-Cyclopentyl-7-methoxy-5,6-dihydro-quinazolin-2-yl)-phenyl-amine;
8-Cyclopentyl-2-phenylamino-5,8-dihydro-quinazolin-7-ol;
(8-Cyclopentyl-7-methoxy-5,8-dihydro-quinazolin-2-yl)-phenyl-amine;
8-Isopropyl-2-(4-pyrrolidin-1-yl-phenylamino)-5,6-dihydro-quinazolin-7-ol;
(8-Isopropyl-7-methoxy-5,6-dihydro-quinazolin-2-yl)-(4-pyrrolidin-1-yl-phenyl)-amine;
8-Isopropyl-2-(4-pyrrolidin-1-yl-phenylamino)-5,8-dihydro-quinazolin-7-ol;
(8-Isopropyl-7-methoxy-5,8-dihydro-quinazolin-2-yl)-(4-pyrrolidin-1-yl-phenyl)-amine;
8-Cyclopentyl-2-(4-pyrrolidin-1-yl-phenylamino)-5,6-dihydro-quinazolin-7-ol;
(8-Cyclopentyl-7-methoxy-5,6-dihydro-quinazolin-2-yl)-(4-pyrrolidin-1-yl-phenyl)-amine;
8-Cyclopentyl-2-(4-pyrrolidin-1-yl-phenylamino)-5,8-dihydro-quinazolin-7-ol;
(8-Cyclopentyl-7-methoxy-5,8-dihydro-quinazolin-2-yl)-(4-pyrrolidin-1-yl-phenyl)-amine;
8-Isopropyl-2-(4-piperazin-1-yl-phenylamino)-5,6-dihydro-quinazolin-7-ol;
(8-Isopropyl-7-methoxy-5,6-dihydro-quinazolin-2-yl)-(4-piperazin-1-yl-phenyl)-amine;
8-Isopropyl-2-(4-piperazin-1-yl-phenylamino)-5,8-dihydro-quinazolin-7-ol;
(8-Isopropyl-7-methoxy-5,8-dihydro-quinazolin-2-yl)-(4-piperazin-1-yl-phenyl)-amine;
8-Cyclopentyl-2-(4-piperazin-1-yl-phenylamino)-5,6-dihydro-quinazolin-7-ol;
(8-Cyclopentyl-7-methoxy-5,6-dihydro-quinazolin-2-yl)-(4-piperazin-1-yl-phenyl)-amine;
8-Cyclopentyl-2-(4-piperazin-1-yl-phenylamino)-5,8-dihydro-quinazolin-7-ol;
(8-Cyclopentyl-7-methoxy-5,8-dihydro-quinazolin-2-yl)-(4-piperazin-1-yl-phenyl)-amine;
2-(4-Fluoro-3-methyl-phenylamino)-8-isopropyl-5,6-dihydro-quinazolin-7-ol;
(4-Fluoro-3-methyl-phenyl)-(8-isopropyl-7-methoxy-5,6-dihydro-quinazolin-2-yl)-amine;
2-(4-Fluoro-3-methyl-phenylamino)-8-isopropyl-5,8-dihydro-quinazolin-7-ol;
(4-Fluoro-3-methyl-phenyl)-(8-isopropyl-7-methoxy-5,8-dihydro-quinazolin-2-yl)-amine;
8-Cyclopentyl-2-(4-fluoro-3-methyl-phenylamino)-5,6-dihydro-quinazolin-7ol;
(8-Cyclopentyl-7-methoxy-5,6-dihydro-quinazolin-2-yl)-(4-fluoro-3-methyl-phenyl)-amine;
8-Cyclopentyl-2-(4-fluoro-3-methyl-phenylamino)-5,8-dihydro-quinazolin-7-ol;
(8-Cyclopentyl-7-methoxy-5,8-dihydro-quinazolin-2-yl)-(4-fluoro-3-methyl-phenyl)-amine;
8-Isopropyl-2-(pyridin-4-ylamino)-5,6-dihydro-quinazolin-7-ol;
(8-Isopropyl-7-methoxy-5,6-dihydro-quinazolin-2-yl)-pyridin-4-yl-amine;
8-Isopropyl-2-(pyridin-4-ylamino)-5,8-dihydro-quinazolin-7-ol;
(8-Isopropyl-7-methoxy-5,8-dihydro-quinazolin-2-yl)-pyridin-4-yl-amine;
8-Cyclopentyl-2-(pyridin-4-ylamino)-5,6-dihydro-quinazolin-7-ol;
(8-Cyclopentyl-7-methoxy-5,6-dihydro-quinazolin-2-yl)-pyridin-4-yl-amine;
8-Cyclopentyl-2-(pyridin-4-ylamino)-5,8-dihydro-quinazolin-7-ol;
(8-Cyclopentyl-7-methoxy-5,8-dihydro-quinazolin-2-yl)-pyridin-4-yl-amine;
2-[4-(3-Amino-pyrrolidin-1-yl)-phenylamino]-8-isopropyl-5,6-dihydro-quinazolin-7-ol;
[4-(3-Amino-pyrrolidin-1-yl)-phenyl]-(8-isopropyl-7-methoxy-5,6-dihydro-quinazolin-2-yl)-amine;
2-[4-(3-Amino-pyrrolidin-1-yl)-phenylamino]-8-isopropyl-5,8-dihydro-quinazolin-7-ol;
[4-(3-Amino-pyrrolidin-1-yl)-phenyl]-(8-isopropyl-7-methoxy-5,8-dihydro-quinazolin-2-yl)-amine;
2-[4-(3-Amino-pyrrolidin-1-yl)-phenylamino]-8-cyclopentyl-5,6-dihydro-quinazolin-7-ol;
[4-(3-Amino-pyrrolidin-1-yl)-phenyl]-(8-cyclopentyl-7-methoxy-5,6-dihydro-quinazolin-2-yl)-amine;
2-[4-(3-Amino-pyrrolidin-1-yl)-phenylamino]-8-cyclopentyl-5,8-dihydro-quinazolin-7-ol;
[4-(3-Amino-pyrrolidin-1-yl)-phenyl]-(8-cyclopentyl-7-methoxy-5,8-dihydro-quinazolin-2-yl)-amine;
8-Isopropyl-2-[4-(5-methyl-hexahydro-pyrrolo[3,4-c]pyrrol-2-yl)-phenylamino]-5,6-dihydro-quinazolin-7-ol;
(8-Isopropyl-7-methoxy-5,6-dihydro-quinazolin-2-yl)-[4-(5-methyl-hexahydro-pyrrolo[ 3,4-c]pyrrol-2-yl)-phenyl]-amine;
8-Isopropyl-2-[4-(5-methyl-hexahydro-pyrrolo[3,4-c]pyrrol-2-yl)-phenylamino]-5,8-dihydro-quinazolin-7-ol;
(8-Isopropyl-7-methoxy-5,8-dihydro-quinazolin-2-yl)-[4-(5-methyl-hexahydro-pyrrolo[ 3,4-c]pyrrol-2-yl)-phenyl]-amine;
8-Cyclopentyl-2-[4-(5-methyl-hexahydro-pyrrolo[3,4-c]pyrrol-2-yl)-phenylamino]-5,6-dihydro-quinazolin-7-ol;
(8-Cyclopentyl-7-methoxy-5,6-dihydro-quinazolin-2-yl)-[4-(5-methyl-hexahydro-pyrrolo[ 3,4-c]pyrrol-2-yl)-phenyl]-amine;
8-Cyclopentyl-2-[4-(5-methyl-hexahydro-pyrrolo[3,4-c]pyrrol-2-yl)-phenylamino]-5,8-dihydro-quinazolin-7-ol;
(8-Cyclopentyl-7-methoxy-5,8-dihydro-quinazolin-2-yl)-[4-(5-methyl-hexahydro-pyrrolo[ 3,4-c]pyrrol-2-yl)-phenyl]-amine;
1-{4-[4-(7-Hydroxy-8-isopropyl-5,6-dihydro-quinazolin-2-ylamino)-phenyl]-piperazin-1-yl}-ethanone;
1-{4-[4-(8-Isopropyl-7-methoxy-5,6-dihydro-quinazolin-2-ylamino)-phenyl]-piperazin-1-yl}-ethanone;
1-{4-[4-(7-Hydroxy-8-isopropyl-5,8-dihydro-quinazolin-2-ylamino)-phenyl]-piperazin-1-yl}-ethanone;
1-{4-[4-(8-Isopropyl-7-methoxy-5,8-dihydro-quinazolin-2-ylamino)-phenyl]-piperazin-1-yl}-ethanone;
1-{4-[4-(8-Cyclopentyl-7-hydroxy-5,6-dihydro-quinazolin-2-ylamino)-phenyl]-piperazin-1-yl}-ethanone;
1-{4-[4-(8-Cyclopentyl-7-methoxy-5,6-dihydro-quinazolin-2-ylamino)-phenyl]-piperazin-1-yl}-ethanone;
1-{4-[4-(8-Cyclopentyl-7-hydroxy-5,8-dihydro-quinazolin-2-ylamino)-phenyl]-piperazin-1-yl}-ethanone;
1-{4-[4-(8-Cyclopentyl-7-methoxy-5,8-dihydro-quinazolin-2-ylamino)-phenyl]-piperazin-1-yl}-ethanone;
1-{4-[4-(7-Hydroxy-8-isopropyl-5,6-dihydro-quinazolin-2-ylamino)-phenyl]-piperazin-1-yl}-propan-1one;
1-{4-[4-(8-Isopropyl-7-methoxy-5,6-dihydro-quinazolin-2-ylamino)-phenyl]-piperazin-1-yl}-propan-1-one;
1-{4-[4-(7-Hydroxy-8-isopropyl-5,8-dihydro-quinazolin-2-ylamino)-phenyl]-piperazin-1-yl}-propan-1-one;
1-{4-[4-(8-Isopropyl-7-methoxy-5,8-dihydro-quinazolin-2-ylamino)-phenyl]-piperazin-1-yl}-propan-1-one;
1-{4-[4-(8-Cyclopentyl-7-hydroxy-5,6-dihydro-quinazolin-2-ylamino)-phenyl]-piperazin-1-yl}-propan-1-one;

1-{4-[4-(8-Cyclopentyl-7-methoxy-5,6-dihydro-quinazolin-2-ylamino)-phenyl]-piperazin-1-yl}-propan-1-one;
1-{4-[4-(8-Cyclopentyl-7-hydroxy-5,8-dihydro-quinazolin-2-ylamino)-phenyl]-piperazin-1-yl}-propan-1-one;
1-{4-[4-(8-Cyclopentyl-7-methoxy-5,8-dihydro-quinazolin-2-ylamino)-phenyl]-piperazin-1-yl}-propan-1-one;
2-Amino-1-{4-[4-(7-hydroxy-8-isopropyl-5,6-dihydro-quinazolin-2-ylamino)-phenyl]-piperazin-1-yl}-3-methyl-butan-1-one;
2-Amino-1-{4-[4-(8-isopropyl-7-methoxy-5,6-dihydro-quinazolin-2-ylamino)-phenyl]-piperazin-1-yl}-3-methyl-butan-1-one;
2-Amino-1-{4-[4-(7-hydroxy-8-isopropyl-5,8-dihydro-quinazolin-2-ylamino)-phenyl]-piperazin-1-yl}-3-methyl-butan-1-one;
2-Amino-1-{4-[4-(8-isopropyl-7-methoxy-5,8-dihydro-quinazolin-2-ylamino)-phenyl]-piperazin-1-yl}-3-methyl-butan-1-one;
2-Amino-1-{4-[4-(8-cyclopentyl-7-hydroxy-5,6-dihydro-quinazolin-2-ylamino)-phenyl]-piperazin-1-yl}-3-methyl-butan-1-one;
2-Amino-1-{4-[4-(8-cyclopentyl-7-methoxy-5,6-dihydro-quinazolin-2-ylamino)-phenyl]-piperazin-1-yl}-3-methyl-butan-1-one;
2-Amino-1-{4-[4-(8-cyclopentyl-7-hydroxy-5,8-dihydro-quinazolin-2-ylamino)-phenyl]-piperazin-1-yl}-3-methyl-butan-1-one;
2-Amino-1-{4-[4-(8-cyclopentyl-7-methoxy-5,8-dihydro-quinazolin-2-ylamino)-phenyl]-piperazin-1-yl}-3-methyl-butan-1-one;
2-Amino-1-{4-[4-(7-hydroxy-8-isopropyl-5,6-dihydro-quinazolin-2-ylamino)-phenyl]-piperazin-1-yl}-4-methyl-pentan-1-one;
2-Amino-1-{4-[4-(8-isopropyl-7-methoxy-5,6-dihydro-quinazolin-2-ylamino)-phenyl]-piperazin-1-yl}-4-methyl-pentan-1-one;
2-Amino-1-{4-[4-(7-hydroxy-8-isopropyl-5,8-dihydro-quinazolin-2-ylamino)-phenyl]-piperazin-1-yl}-4-methyl-pentan-1-one;
2-Amino-1-{4-[4-(8-isopropyl-7-methoxy-5,8-dihydro-quinazolin-2-ylamino)-phenyl]-piperazin-1-yl}-4-methyl-pentan-1-one;
2-Amino-1-{4-[4-(8-cyclopentyl-7-hydroxy-5,6-dihydro-quinazolin-2-ylamino)-phenyl]-piperazin-1-yl}-4-methyl-pentan-1-one;
2-Amino-1-{4-[4-(8-cyclopentyl-7-methoxy-5,6-dihydro-quinazolin-2-ylamino)-phenyl]-piperazin-1-yl}-4-methyl-pentan-1-one;
2-Amino-1-{4-[4-(8-cyclopentyl-7-hydroxy-5,8-dihydro-quinazolin-2-ylamino)-phenyl]-piperazin-1-yl}-4-methyl-pentan-1-one;
2-Amino-1-{4-[4-(8-cyclopentyl-7-methoxy-5,8-dihydro-quinazolin-2-ylamino)-phenyl]-piperazin-1-yl}-4-methyl-pentan-1-one;
2-Amino-1-{4-[4-(7-hydroxy-8-isopropyl-5,6-dihydro-quinazolin-2-ylamino)-phenyl]-piperazin-1-yl}-ethanone;
2-Amino-1-{4-[4-(8-isopropyl-7-methoxy-5,6-dihydro-quinazolin-2-ylamino)-phenyl]-piperazin-1-yl}-ethanone;
2-Amino-1-{4-[4-(7-hydroxy-8-isopropyl-5,8-dihydro-quinazolin-2-ylamino)-phenyl]-piperazin-1-yl}-ethanone;
2-Amino-1-{4-[4-(8-isopropyl-7-methoxy-5,8-dihydro-quinazolin-2-ylamino)-phenyl]-piperazin-1-yl}-ethanone;
2-Amino-1-{4-[4-(8-cyclopentyl-7-hydroxy-5,6-dihydro-quinazolin-2-ylamino)-phenyl]-piperazin-1-yl}-ethanone;
2-Amino-1-{4-[4-(8-cyclopentyl-7-methoxy-5,6-dihydro-quinazolin-2-ylamino)-phenyl]-piperazin-1-yl}-ethanone;
2-Amino-1-{4-[4-(8-cyclopentyl-7-hydroxy-5,8-dihydro-quinazolin-2-ylamino)-phenyl]-piperazin-1-yl}-ethanone;
2-Amino-1-{4-[4-(8-cyclopentyl-7-methoxy-5,8-dihydro-quinazolin-2-ylamino)-phenyl]-piperazin-1-yl}-ethanone;
(4-Fluoro-3-methyl-phenyl)-(8-isopropyl-7-methoxy-quinazolin-2-yl)-amine;
2-(4-Fluoro-3-methyl-phenylamino)-8-isopropyl-quinazolin-7-ol;
(8-Cyclopentyl-7-methoxy-quinazolin-2-yl)-(4-fluoro-3-methyl-phenyl)-amine;
8-Cyclopentyl-2-(4-fluoro-3-methyl-phenylamino)-quinazolin-7-ol;
(3-Chloro-4-fluoro-phenyl)-(8-isopropyl-7-methoxy-quinazolin-2-yl)-amine;
2-(3-Chloro-4-fluoro-phenylamino)-8-isopropyl-quinazolin-7-ol;
(3-Chloro-4-fluoro-phenyl)-(8-cyclopentyl-7-methoxy-quinazolin-2-yl)-amine;
2-(3-Chloro-4-fluoro-phenylamino)-8-cyclopentyl-quinazolin-7-ol;
(3,4-Difluoro-phenyl)-(8-isopropyl-7-methoxy-quinazolin-2-yl)-amine;
2-(3,4-Difluoro-phenylamino)-8-isopropyl-quinazolin-7-ol;
(8-Cyclopentyl-7-methoxy-quinazolin-2-yl)-(3,4-difluoro-phenyl)-amine;
8-Cyclopentyl-2-(3,4-difluoro-phenylamino)-quinazolin-7-ol;
(3-Fluoro-4-piperazin-1-yl-phenyl)-(8-isopropyl-7-methoxy-quinazolin-2-yl)-amine;
2-(3-Fluoro-4-piperazin-1-yl-phenylamino)-8-isopropyl-quinazolin-7-ol;
(8-Cyclopentyl-7-methoxy-quinazolin-2-yl)-(3-fluoro-4-piperazin-1-yl-phenyl)-amine;
8-Cyclopentyl-2-(3-fluoro-4-piperazin-1-yl-phenylamino)-quinazolin-7-ol;
[4-(3-Amino-pyrrolidin-1-yl)-3-fluoro-phenyl]-(8-isopropyl-7-methoxy-quinazolin-2-yl)-amine;
2-[4-(3-Amino-pyrrolidin-1-yl)-3-fluoro-phenylamino]-8-isopropyl-quinazolin-7-ol;
[4-(3-Amino-pyrrolidin-1-yl)-3-fluoro-phenyl]-(8-cyclopentyl-7-methoxy-quinazolin-2-yl)-amine;
2-[4-(3-Amino-pyrrolidin-1-yl)-3-fluoro-phenylamino]-8-cyclopentyl-quinazolin-7-ol;
{3-Fluoro-4-[4-(3-morpholin-4-yl-propyl)-piperidin-1-yl]-phenyl}-(8-isopropyl-7-methoxy-quinazolin-2-yl)-amine;
2-{3-Fluoro-4-[4-(3-morpholin-4-yl-propyl)-piperidin-1-yl]-phenylamino}-8-isopropyl-quinazolin-7-ol;
(8-Cyclopentyl-7-methoxy-quinazolin-2-yl)-{3-Fluoro-4-[4-(3-morpholin-4-yl-propyl)-piperidin-1-yl]-phenyl}-amine;
8-Cyclopentyl-2-{3-fluoro-4-[4-(3-morpholin-4-yl-propyl)-piperidin-1-yl]-phenylamino}-quinazolin-7-ol;
(8-Isopropyl-7-methoxy-quinazolin-2-yl)-{4-[4-(3-morpholin-4-yl-propyl)-piperidin-1-yl]-phenyl}-amine;
8-Isopropyl-2-{4-[4-(3-morpholin-4-yl-propyl)-piperidin-1-yl]-phenylamino}-quinazolin-7-ol;
(8-Cyclopentyl-7-methoxy-quinazolin-2-yl)-{4-[4-(3-morpholin-4-yl-propyl)-piperidin-1-yl]-phenyl}-amine;

8-Cyclopentyl-2-{4-[4-(3-morpholin-4-yl-propyl)-piperidin-1-yl]-phenylamino}-quinazolin-7-ol;
(8-Isopropyl-7-methoxy-quinazolin-2-yl)-{4-[4-(3-piperazin-1-yl-propyl)-piperidin-1-yl]-phenyl}-amine;
8-Isopropyl-2-{4-[4-(3-piperazin-1-yl-propyl)-piperidin-1-yl]-phenylamino}-quinazolin-7-ol;
(8-Cyclopentyl-7-methoxy-quinazolin-2-yl)-{4-[4-(3-piperazin-1-yl-propyl)-piperidin-1-yl]-phenyl}-amine;
8-Cyclopentyl-2-{4-[4-(3-piperazin-1-yl-propyl)-piperidin-1-yl]-phenylamino}-quinazolin-7-ol;
{3-Chloro-4-[4-(3-piperazin-1-yl-propyl)-piperidin-1-yl]-phenyl}-(8-isopropyl-7-methoxy-quinazolin-2-yl)-amine;
2-{3-Chloro-4-[4-(3-piperazin-1-yl-propyl)-piperidin-1-yl]-phenylamino}-8-isopropyl-quinazolin-7-ol;
{3-Chloro-4-[4-(3-piperazin-1-yl-propyl)-piperidin-1-yl]-phenyl}-(8-cyclopentyl-7-methoxy-quinazolin-2-yl)-amine;
2-{3-Chloro-4-[4-(3-piperazin-1-yl-propyl)-piperidin-1-yl]-phenylamino}-8-cyclopentyl-quinazolin-7-ol;
(3-Fluoro-4-{4-[3-(1H-tetrazol-5-yl)-propyl]-piperidin-1-yl}-phenyl)-(8-isopropyl-7-methoxy-quinazolin-2-yl)-amine;
2-(3-Fluoro-4-{4-[3-(1H-tetrazol-5-yl)-propyl]-piperidin-1-yl}-phenylamino)-8-isopropyl-quinazolin-7-ol;
(8-Cyclopentyl-7-methoxy-quinazolin-2-yl)-(3-fluoro-4-{4-[3-(1H-tetrazol-5-yl)-propyl]-piperidin-1-yl}-phenyl)-amine;
8-Cyclopentyl-2-(3-fluoro-4-{4-[3-(1H-tetrazol-5-yl)-propyl]-piperidin-1-yl}-phenylamino)-quinazolin-7-ol;
(4-{4-[3-(3-Amino-pyrrolidin-1-yl)-propyl]-piperidin-1-yl}-3-chloro-phenyl)-( 8-isopropyl-7-methoxy-quinazolin-2-yl)-amine;
2-(4-{4-[3-(3-Amino-pyrrolidin-1-yl)-propyl]-piperidin-1-yl}-3-chloro-phenylamino)-8-isopropyl-quinazolin-7-ol;
(4-{4-[3-(3-Amino-pyrrolidin-1-yl)-propyl]-piperidin-1-yl}-3-chloro-phenyl)-( 8-cyclopentyl-7-methoxy-quinazolin-2-yl)-amine;
2-(4-{4-[3-(3-Amino-pyrrolidin-1-yl)-propyl]-piperidin-1-yl}-3-chloro-phenylamino)-8-cyclopentyl-quinazolin-7-ol;
(4-{4-[3-(3-Amino-pyrrolidin-1-yl)-propyl]-piperidin-1-yl}-phenyl-(8-isopropyl-7-methoxy-quinazolin-2-yl)-amine;
2-(4-{4-[3-(3-Amino-pyrrolidin-1-yl)-propyl]-piperidin-1-yl}-phenylamino)-8-isopropyl-quinazolin-7-ol;
(4-{4-[3-(3-Amino-pyrrolidin-1-yl)-propyl]-piperidin-1-yl}-phenyl)-(8-cyclopentyl-7-methoxy-quinazolin-2-yl)-amine;
2-(4-{4-[3-(3-Amino-pyrrolidin-1-yl)-propyl]-piperidin-1-yl}-phenylamino)-8-cyclopentyl-quinazolin-7-ol;
(8-Isopropyl-7-methoxy-quinazolin-2-yl)-{4-[4-(4-methoxy-phenyl)-piperazin-1-yl]-phenyl}-amine;
8-Isopropyl-2-{4-[4-(4-methoxy-phenyl)-piperazin-1-yl]-phenylamino}-quinazolin-7-ol;
(8-Cyclopentyl-7-methoxy-quinazolin-2-yl)-{4-[4-(4-methoxy-phenyl)-piperazin-1-yl]-phenyl}-amine;
8-Cyclopentyl-2-{4-[4-(4-methoxy-phenyl)-piperazin-1-yl]-phenylamino}-quinazolin-7-ol;
(8-Isopropyl-7-methoxy-quinazolin-2-yl)-[4-(3,3,4-trimethyl-piperazin-1-yl)-phenyl]-amine;
8-Isopropyl-2-[4-(5-methyl-hexahydro-pyrrolo[3,4-c]pyrrol-2-yl)-phenylamino]-quinazolin-7-ol;
(8-Cyclopentyl-7-methoxy-quinazolin-2-yl)-[4-(5-methyl-hexahydro-pyrrolo[ 3,4-c]pyrrol-2-yl)-phenyl]-amine;
8-Cyclopentyl-2-[4-(5-methyl-hexahydro-pyrrolo[3,4-c]pyrrol-2-yl)-phenylamino]-quinazolin-7-ol;
(8-Isopropyl-2-[4-(3,3,4-trimethyl-piperazin-1-yl)-phenylamino]-quinazolin-7-ol;
(8-Cyclopentyl-7-methoxy-quinazolin-2-yl)-[4-(3,3,4-trimethyl-piperazin-1yl)-phenyl]-amine;
8-Cyclopentyl-2-[4-(3,3,4-trimethyl-piperazin-1-yl)-phenylamino]-quinazolin-7-ol;
(8-Isopropyl-7-methoxy-quinazolin-2-yl)-[4-(5-methyl-hexahydro-pyrrolo[ 3,4-c]pyrrol-2-yl)-phenyl]-amine;
(8-Cyclopentyl-7-methoxy-quinazolin-2-yl)-(4-perhydro-1,4-diazepin-1-yl-phenyl)-amine;
8-Cyclopentyl-2-(4-perhydro-1,4-diazepin-1-yl-phenylamino)-quinazolin-7-ol;
2-{4-[4-(8-Cyclopentyl-7-methoxy-quinazolin-2-ylamino)-phenyl]-2,6-dimethyl-piperazin-1-yl}-ethanol;
(8-Cyclopentyl-7-methoxy-quinazolin-2-yl)-[4-(2-methylamino-ethoxy)-phenyl]-amine;
1-{4-[4-(8-Cyclopentyl-7-methoxy-quinazolin-2-ylamino)-phenyl]-perhydro-1,4-diazepin-1-yl}-ethanone;
8-Cyclopentyl-2-[4-(3,3-dimethyl-piperazin-1-yl)-phenylamino]-quinazolin-7-ol;
(8-Cyclopentyl-7-methoxy-quinazolin-2-yl)-[4-(3,3-dimethyl-piperazin-1-yl)-phenyl]-amine;
1-{4-[4-(8-Cyclopentyl-7-hydroxy-quinazolin-2-ylamino)-phenyl]-perhydro-1,4-diazepin-1-yl}-ethanone;
(8-Cyclopentyl-7-methoxy-quinazolin-2-yl)-(4-{4-[3-(1H-tetrazol-5-yl)-propyl]-piperidin-1-yl}-phenyl)-amine;
8-Cyclopentyl-2-(4-{4-[3-(1H-tetrazol-5-yl)-propyl]-piperidin-1-yl}-phenylamino)-quinazolin-7-ol;
8-Cyclopentyl-$N^2$-(4-piperazin-1-yl-phenyl)-quinazoline-2,7-diamine;
8-Cyclopentyl-$N^2$-[4-(4-methyl-piperazin-1-yl)-phenyl]-quinazoline-2,7-diamine;
1-{4-[4-(7-Amino-8-cyclopentyl-quinazolin-2-ylamino)-phenyl]-piperazin-1-yl}-ethanone;
8-Cyclopentyl-$N^2$-(4-perhydro-1,4-diazepin-1-yl-phenyl)-quinazoline-2,7-diamine;
8-Cyclopentyl-$N^2$-[4-(3,3-dimethyl-piperazin-1-yl)-phenyl]-quinazoline-2,7-diamine;
8-Cyclopentyl-$N^7$-methyl-$N^2$-(4-piperazin-1-yl-phenyl)-quinazoline-2,7-diamine;
8-Cyclopentyl-$N^7$-methyl-$N^2$-[4-(4-methyl-piperazin-1-yl)-phenyl]-quinazoline-2,7-diamine;
1-{4-[4-(8-Cyclopentyl-7-methylamino-quinazolin-2-ylamino)-phenyl]-piperazin-1-yl}-ethanone;
8-Cyclopentyl-$N^7$-methyl-$N^2$-[4-perhydro-1,4-diazepin-1-yl-phenyl)-quinazoline-2,7-diamine;
8-Cyclopentyl-$N^2$-[4-(3,3-dimethyl-piperazin-1-yl)-phenyl]-$N^7$-methyl-quinazoline-2,7-diamine;
8-Cyclopentyl-$N^7,N^7$-dimethyl-$N^2$-(4-piperazin-1-yl-phenyl)-quinazoline-2,7-diamine;
8-Cyclopentyl-$N^7,N^7$-dimethyl-$N^2$-[4-(4-methyl-piperazin-1-yl)-phenyl]-quinazoline-2,7-diamine;
1-{4-[4-(8-Cyclopentyl-7-dimethylamino-quinazolin-2-ylamino)-phenyl]-piperazin-1-yl}-ethanone;
8-Cyclopentyl-$N^7,N^7$-dimethyl-$N^2$-(4-perhydro-1,4-diazepin-1-yl-phenyl)-quinazoline-2,7-diamine;
8-Cyclopentyl-$N^2$-[4-(3,3-dimethyl-piperazin-1-yl)-phenyl]-$N^7,N^7$-dimethyl-quinazoline-2,7-diamine;
8-Cyclopentyl-$N^2$-(4-{4-[3-(1H-tetrazol-5-yl)-propyl]-piperidin-1-yl}-phenyl)-quinazoline-2,7-diamine;
8-Cyclopentyl-$N^7$-methyl-$N^2$-(4-{4-[3-(1H-tetrazol-5-yl)-propyl]-piperidin-1-yl}-phenyl)-quinazoline-2,7-diamine;
8-Cyclopentyl-$N^2$-{4-[4-(3-piperazin-1-yl-propyl)-piperidin-1-yl]-phenyl}-quinazoline-2,7-diamine;
8-Cyclopentyl-$N^7$-methyl-$N^2$-{4-[4-(3-piperazin-1-yl-propyl)-piperidin-1-yl]-phenyl}-quinazoline-2,7-diamine;

8-Cyclopentyl-N⁷,N⁷-dimethyl-N²-{4-[4-(3-piperazin-1-yl-propyl)-piperidin-1-yl]-phenyl}-quinazoline-2,7-diamine;
(8-Cyclopentyl-7-methoxy-5-methyl-quinazolin-2-yl)-(4-perhydro-1,4-diazepin-1-yl-phenyl)-amine;
8-Cyclopentyl-5-methyl-2-(4-perhydro-1,4-diazepin-1-yl-phenylamino)-quinazolin-7-ol;
2-{4-[4-(8-Cyclopentyl-7-methoxy-5-methyl-quinazolin-2-ylamino)-phenyl] -2,6-dimethyl-piperazin-1-yl}-ethanol;
(8-Cyclopentyl-7-methoxy-5-methyl-quinazolin-2-yl)-[4-(2-methylamino-ethoxy)-phenyl] -amine;
1-{4-[4-(8-Cyclopentyl-7-methoxy-5-methyl-quinazolin-2-ylamino)-phenyl]    -perhydro-1,4-diazepin-1-yl}-ethanone;
8-Cyclopentyl-2-[4-(3,3-dimethyl-piperazin-1-yl)-phenylamino]-5-methyl-quinazolin-7-ol;
(8-Cyclopentyl-7-methoxy-5-methyl-quinazolin-2-yl)-[4-(3,3-dimethyl-piperazin-1-yl)-phenyl]-amine;
1-{4-[4-(8-Cyclopentyl-7-hydroxy-5-methyl-quinazolin-2-ylamino)-phenyl]   -perhydro-1,4-diazepin-1-yl}-ethanone;
(8-Cyclopentyl-7-methoxy-5-methyl-quinazolin-2-yl)-(4-{4-[4-(1H-tetrazol-5-yl)-propyl]-piperidin-1-yl}-phenyl)-amine;
8-Cyclopentyl-5-methyl-2-(4-{4-[3-(1H-tetrazol-5-yl)-propyl]-piperidin-1-yl}-phenylamino)-quinazolin-7-ol;
1-{4-[4-(8-Cyclopentyl-7-hydroxy-5-methyl-quinazolin-2-ylamino)-phenyl] -piperazin-1-yl}-ethanone;
1-{4-[4-(8-Cyclopentyl-7-methoxy-5-methyl-quinazolin-2-ylamino)-phenyl] -piperazin-1-yl}-ethanone;
8-Cyclopentyl-5-methyl-2-(4-piperazin-1-yl-phenylamino)-quinazolin-7-ol;
(8-Cyclopentyl-7-methoxy-5-methyl-quinazolin-2-yl)-(4-piperazin-1-yl-phenyl)-amine;
(8-Cyclopentyl-7-methoxy-5-methyl-quinazolin-2-yl)-{4-[4-(3-piperazin-1-yl-propyl)-piperidin-1-yl]-phenyl}-amine;
(8-Cyclopentyl-5-methyl-2-{4-[4-(3-piperazin-1-yl-propyl)-piperidin-1-yl] -phenylamino}-quinazolin-7-ol;
8-Cyclopentyl-5-methyl-N²-(4-piperazin-1-yl-phenyl)-quinazoline-2,7-diamine;
8-Cyclopentyl-5-methyl-N²-[4-(4-methyl-piperazin-1-yl)-phenyl] -quinazoline-2,7-diamine;
1-{4-[4-(7-Amino-8-cyclopentyl-5-methyl-quinazolin-2-ylamino)-phenyl] -piperazin-1-yl}-ethanone;
8-Cyclopentyl-5-methyl-N²-(4-perhydro-1,4-diazepin-1-yl-phenyl)-quinazolin-2,7-diamine;
8-Cyclopentyl-N²-[4-(3,3-dimethyl-piperazin-1-yl)-phenyl]-5-methyl-quinazoline-2,7-diamine;
8-Cyclopentyl-5,N⁷-dimethyl-N²-(4-piperazin-1-yl-phenyl)-quinazoline-2,7-diamine;
8-Cyclopentyl-5,N⁷-dimethyl-N²-[4-(4-methyl-piperazin-1-yl)-phenyl] -quinazoline-2,7-diamine;
1-{4-[4-(8-Cyclopentyl-5-methyl-7-methylamino-quinazolin-2-ylamino)-phenyl] -piperazin-1-yl}-ethanone;
8-Cyclopentyl-5,N⁷-dimethyl-N²-(4-perhydro-1,4-diazepin-1-yl-phenyl)-quinazoline-2,7-diamine;
8-Cyclopentyl-N²-[4-(3,3-dimethyl-piperazin-1-yl)-phenyl]-5,N⁷-dimethyl--quinazoline-2,7-diamine;
8-Cyclopentyl-5,N⁷,N⁷-trimethyl-N²-(4-piperazin-1-yl-phenyl)-quinazoline-2,7-diamine;
8-Cyclopentyl-5,N⁷,N⁷-trimethyl-N²-[4-(4-methyl-piperazin-1-yl)-phenyl] -quinazoline-2,7-diamine;
1-{4-[4-(8-Cyclopentyl-7-dimethylamino-5-methyl-quinazolin-2-ylamino)-phenyl]-piperazin-1-yl}-ethanone;

8-Cyclopentyl-5,N⁷,N⁷-trimethyl-N²-(4-perhydro-1,4-diazepin-1-yl-phenyl-quinazolin-2,7-diamine;
8-Cyclopentyl-N²-[4-(3,3-dimethyl-piperazin-1-yl)-phenyl]-5,N⁷,N⁷-trimethyl-quinazoline-2,7-diamine;
8-Cyclopentyl-5-methyl-N²-(4-{4-[3-(1H-tetrazol-5-yl)-propyl]-piperidin-1-yl}-phenyl)-quinazoline-2,7-diamine;
8-Cyclopentyl-5,N⁷-dimethyl-N²-(4-{4-[3-(1H-tetrazol-5-yl)-propyl]   -piperidin-1-yl}-phenyl)-quinazoline-2,7-diamine;
8-Cyclopentyl-5-methyl-N²-{4-[4-(3-piperazin-1-yl-propyl)-piperidin-1-yl]-phenyl}-quinazoline-2,7-diamine;
8-Cyclopentyl-5,N⁷-dimethyl-N²-{4-[4-(3-piperazin-1-yl-propyl)-piperidin-1-yl]-phenyl}-quinazoline-2,7-diamine; and
8-Cyclopentyl-5,N⁷,N⁷-trimethyl-N²-{4-[4-(3-piperazin-1-yl-propyl)-piperidin-1-yl]-phenyl}-quinazoline-2,7-diamine.

Additional preferred embodiments of the present invention include those in Examples 1–10, 85, 54, and 57, infra.

Compounds of Formula I wherein $R^2$ is alkyl, $R^5$ and $R^6$ are hydrogen are especially useful as intermediates leading to compounds that display good inhibitory activity against cyclin-dependent kinases. Other especially useful intermediates leading to compounds that display good inhibitory activity against cyclin-dependent kinases are compounds of Formula III

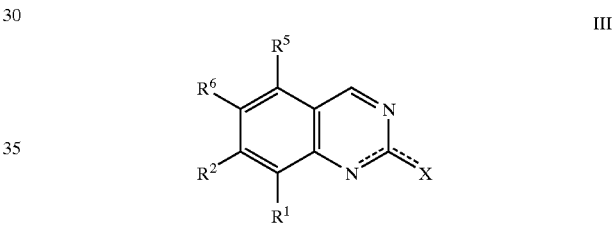

III wherein $R^1$, $R^2$, $R^5$, and $R^6$ are as defined above and X is oxygen or halogen. Particularly useful intermediates are those wherein $R^2$ is alkyloxy, $R^5$ is hydrogen or alkyl, $R^6$ is hydrogen, and $R^8$ is oxygen or chlorine or a pharmaceutically acceptable salt, ester, amide, or pro-drug thereof.

The present invention also discloses processes for preparing compounds of Formula I, II and III. These processes are described by the nonlimiting examples set forth below.

Unless otherwise expressly stated, the following definitions are adhered to throughout this disclosure.

"Alkyl" means a straight or branched hydrocarbon radical having from 1 to 10 carbon atoms (unless stated otherwise) and includes, for example, methyl, ethyl, n-propyl, isopropyl, n-butyl, sec-butyl, isobutyl, tert-butyl, n-pentyl, isopentyl, n-hexyl, and the like. "Halo" includes fluoro, chloro, bromo, and iodo.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or $NR_2$, examples being substituted or unsubstituted oxiranyl, pyrrolidinyl, piperidyl, tetrahydropyran, piperazinyl, acylpiperazinyl, pyrrolidinyl, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$CH_3$, and the like.

"Alkanoyl" groups are alkyl linked through a carbonyl, ie, $C_1$-$C_5$—C(O)—. Such groups include formyl, acetyl, propionyl, butyryl, and isobutyryl.

"Acyl" means an alkyl or aryl (Ar) group bonded through a carbonyl group, ie, R—C(O)—. For example, acyl includes a $C_1$-$C_6$ alkanoyl, including substituted alkanoyl, wherein the alkyl portion can be substituted by $NR^4R^5$ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from $NR^4R^5$, phenyl, substituted phenyl, thio $C_1$-$C_6$ alkyl, $C_1$-$C_6$ alkoxy, hydroxy, carboxy, $C_1$-$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$-$C_6$ alkyl or $(CH_2)_n$Ph where n is 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like.

Preferred Ar groups are phenyl and phenyl substituted by 1, 2, or 3 groups independently selected from the group consisting of alkyl, alkoxy, thio, thioalkyl, hydroxy, —$COOR^7$, amino of formula —$NR^4R^5$, and $T(CH_2)_mQR^4$ or $T(CH_2)_mCO_2R^4$ wherein m is 1 to 6, T is O, S, $NR^4$, $N(O)R^4$, $NR^4R^6Y$, or $CR^4R^5$, Q is O, S, $NR^5$, $N(O)R^5$, or $NR^5R^6Y$ wherein $R^4$ and $R^5$ are as described above, and $R^7$ is alkyl or substituted alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The symbol "—" means a bond.

The term "patient" means all animals including humans. Examples of patients include humans, cows, dogs, cats, goats, sheep, and pigs.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formulas I, II, and III are capable of further forming both pharmaceutically acceptable formulations comprising salts, esters, amides, and prodrugs. As used herein, the term "pharmaceutically acceptable salts, esters, amides, and prodrugs" refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed and including, but not limited to, acid addition and/or base salts, solvents and N-oxides of a compound of Formulas I, II, and III. This invention also provides pharmaceutical formulations comprising a compound of Formulas I, II, or III together with a pharmaceutically acceptable carrier, diluent, or excipient therefor. All of these forms are within the present invention.

Pharmaceutically acceptable acid addition salts of the compounds of Formulas I, II and III include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science,* 1977; 66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Examples of pharmaceutically acceptable, non-toxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to benzyl. $C_1$–$C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "pro-drug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

A therapeutically effective amount is an amount of a compound of Formulas I, II, or III, that when administered to a patient, ameliorates a symptom of the disease.

The term "cardiovascular disorders and diseases" includes, but is not limited to atherosclerosis, psoriasis, and restenosis. Those skilled in the art are easily able to identify patients having atherosclerosis, psoriasis, restenosis, or at risk of having atherosclerosis or restenosis. For example, patients who are at risk of having restenosis include, but are not limited to, patients having undergone balloon angioplasty or other surgical vascular procedures.

The term "cancer" includes, but is not limited to, the following cancers: breast; ovary; cervix; prostate; testis; esophagus; glioblastoma; neuroblastoma; stomach; skin, keratoacanthoma; lung, epidermoid carcinoma, large cell carcinoma, adenocarcinoma; bone; colon, adenocarcinoma, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

The term autoimmune disease includes, but is not limited to inflammation, such as rheumatoid arthritis, and organ graft rejections.

The term kidney disease includes, but is not limited to kidney disease, such as polycystic kidney disease.

Compounds within the scope of the present invention effectively inhibit vascular smooth muscle cell proliferation and migration. The method entails inhibiting vascular smooth muscle proliferation, and/or migration by administering an effective amount of a compound of Formulas I, II, or III to a subject in need of treatment.

The compounds of the present invention are useful for treating cancer (for example, leukemia and cancer of the lung, breast, prostate, and skin such as melanoma), cardiovascular disorders and diseases, infections, autoimmune diseases, gout, kidney diseases, and neurodegenerative diseases and disorders. To utilize a compound of the present invention to treat these indications, a patient having the indication is administered a therapeutically effective amount of a pharmaceutically acceptable composition comprising an invention compound.

The term "neurological disease and disorders" includes, but is not limited to, Alzheimer's disease. Compounds within the scope of the present invention effectively inhibit the degradation of neurons. The method entails inhibiting neural degeneration by administering an effective amount of a compound of Formulas I, II, or III to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, either a compound of Formulas I, II, or III or a corresponding pharmaceutically acceptable salt or solvate of a compound of Formulas I, II, or III.

A further embodiment of this invention is a pharmaceutical formulation comprising a compound of Formulas I, II, or III together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformally over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formulas I, II, or III will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formulas I, II, or III is administered a dosage of about 1 to about 500 mg per day, either singly or in multiple doses over a 24-hour period.

The compounds of the present invention are capable of binding to and inhibiting the activity of proteins having the ability to phosphorylate other proteins, such as cdks. Cdks form complexes with cyclins, and these complexes phosphorylate key proteins allowing cells to proceed through the cell cycle (Meijer L., *Progress in Cell Cycle Research,* 1995;1:351–363). The compounds of this invention inhibit this phosphorylation and therefore can be used as antiproliferative agents for the treatment of cancer and/or restenosis and other proliferative diseases, and as anti-neural degenerative agents for the treatment of neural degenerative disorders such as Alzheimer's disease.

Because of their inhibitory activity against cdks and other kinases, the compounds of the present invention are also useful research tools for studying the mechanism of action of those kinases, both in vitro and in vivo.

While the forms of the invention herein constitute presently preferred embodiments, many others are possible. It is not intended herein to mention all of the possible equivalent forms or ramifications of the invention. It is understood that the terms used herein are merely descriptive rather than limiting, and those skilled in the art will realize that various changes may be made without departing from the spirit or scope of the invention.

Compounds of Formulas I, II, and III may be prepared according to the syntheses outlined in Scheme 1, infra. Although this scheme often indicates exact structures, those with ordinary skill in the art will appreciate that the methods apply widely to analogous compounds of Formulas I, II, and III, given appropriate consideration to protection and deprotection or reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups and methods for attaching and cleaving them are described fully by Greene and Wuts in *Protective Groups in Organic Synthesis,* John Wiley and Sons, New York, (2nd Ed., 1991), and McOmie, *Protective Groups in Organic Chemistry,* Plenum Press, New York, 1973.

Scheme 1 describes a typical method for the preparation of the quinazoline compounds of the invention.

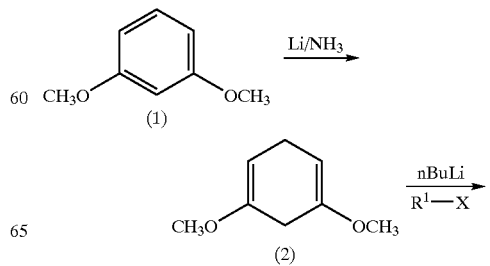

-continued
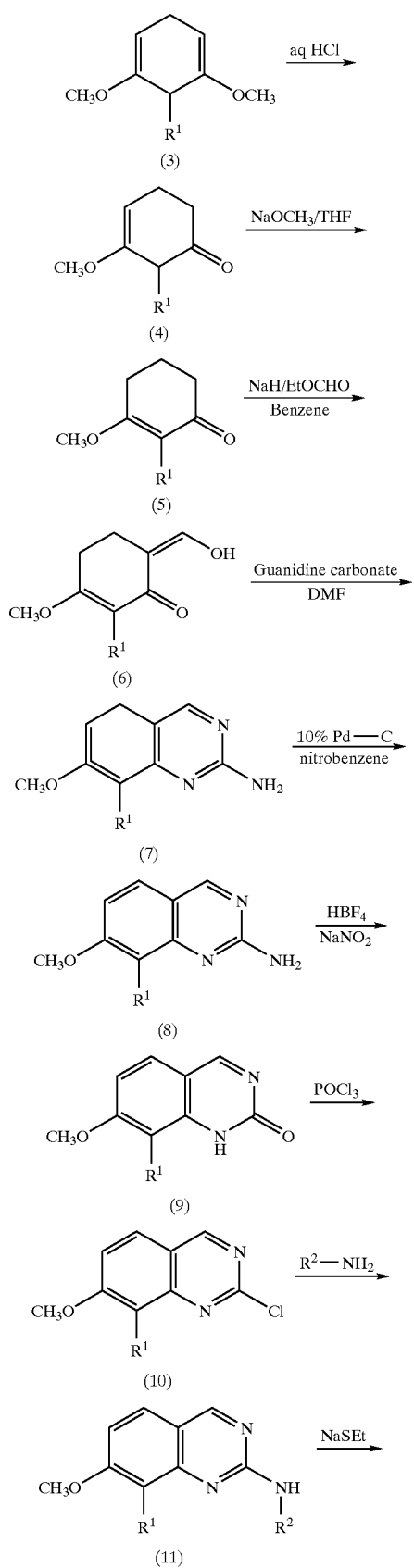
-continued
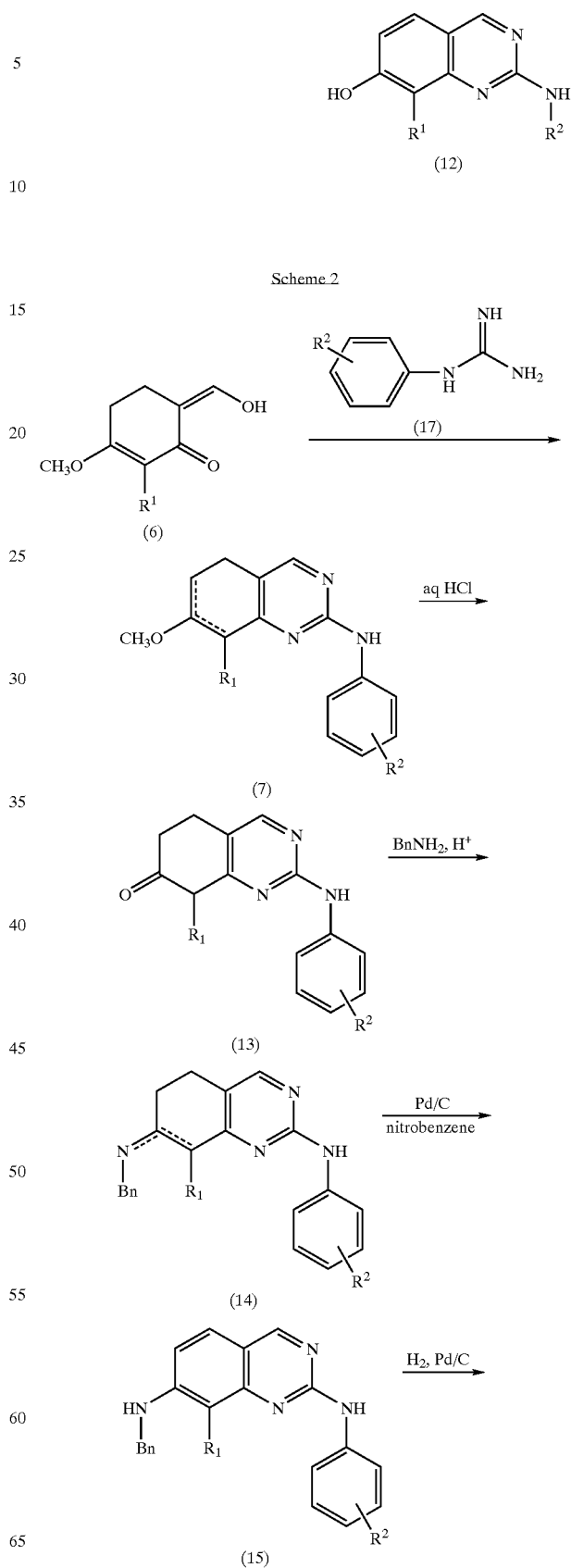

-continued

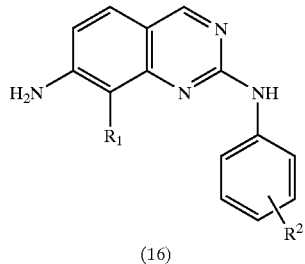

(16)

Scheme 3

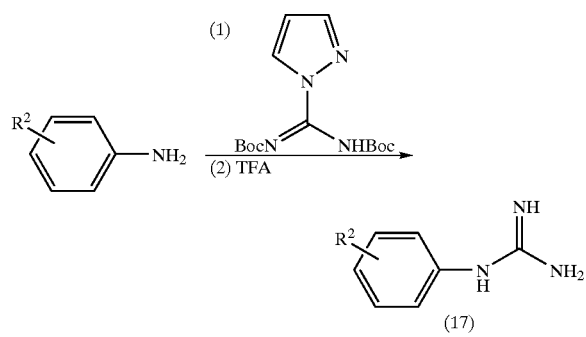

(ref Bernatowivz et al
Tetrahedron Lett. 1993, 34, 3389)

EXAMPLES

The following examples are for illustrative purposes only and are not intended, nor should they be construed as limiting the invention in any manner. Those skilled in the art will appreciate that variations and modifications can be made without violating the spirit or scope of the invention.

Example 1

1,5-Dimethoxy-cyclohexa-1,4-diene

A solution containing 1,3-dimethoxybenzene (10 g), dry THF (15 mL) and 'BuOH (15 mL) was added to distilled ammonia (ca 250 mL). To the reaction mixture was added lithium wire (1.5 g) in small portions, and the deep blue colored solution was stirred for 3 hours. The reaction mixture was decolorized by dropwise addition of methanol. Ammonia was evaporated at room temperature. To the residue, ammonium chloride solution was added, then the product was extracted with hexane (3×120 mL). The combined extracts were washed with water and dried over anhydrous sodium sulfate. Removal of the solvent under reduced pressure gave the title compound as a clear liquid (9.5 g). $^1$H NMR (CDCl$_3$): δ 2.7–2.9 (m, 4H, 2×CH$_2$), 3.58 (s, 6H, 2×OCH$_3$), 4.66 (t, 2H, olefinic).

Example 2

6-Isopropyl-1,5-dimethoxy-cyclohexa-1,4-diene

To a solution of 1,5-dimethoxy-cyclohexa-1,4diene (7 g, 50 mmol) in dry THF (140 mL) was added dropwise nBuLi solution (2.5 M, 30 mL) in hexane at −20° C. The orange colored reaction mixture was stirred for 0.5 hours at −20° C., then isopropyl iodide (17 g, 100 mmol) was added dropwise. The reaction mixture was stirred for 1 hour, while the temperature was raised to 0° C. Excess nBuLi was destroyed cautiously with methanol. Cold water (140 mL) was added to the reaction mixtures, then the product was extracted with ethyl acetate (3×70 mL). The combined organic extracts were washed with brine, dried over anhydrous sodium sulfate, and concentrated to give the title compound as a light yellow liquid (8.5 g, 93.4%). $^1$H NMR CDCl$_3$): δ 0.90 (d, 6H, 2×CH$_3$), 2.1 (m, 1H, CH), 2.76 (m, 3H, CH$_2$ and CH), 3.53 (s, 6H, 2×OCH$_3$), 4.73 (t, 2H, olefinic).

Example 3

2-Isopropyl-3-methoxy-cyclohex-3-enone

To a solution of 6-isopropyl-1,5dimethoxy-cyclohexa-1,4-diene (7 g) in methanol (50 mL) was added 2.5% hydrochloric acid (10 mL) drop wise at 0° C. The reaction mixture was stirred for 45 minutes, then diluted with ice-cold water (30 mL). The product was extracted with ether (3×70 mL). The combined organic extracts were washed with brine and dried over anhydrous sodium sulfate. Removal of the solvent in vacuo yielded the title compound as a light yellow oil (6 g, 93%).

Example 4

2-Isopropyl-3-methoxy-cyclohex-2-enone

To a solution of 2-isopropyl-3-methoxy-cyclohex-3-enone (6 g) in dry THF (120 mL), sodium methoxide (1.5 g) was added in portions at room temperature. After stirring at room temperature for 1.5 hours, the reaction mixture was cooled in an ice bath and neutralized with 10% sodium hydrogen phosphate solution. The organic layer was separated, then the aqueous layer was extracted with ethyl acetate (2×50 mL). The combined organic extracts were washed with brine, then dried over anhydrous sodium sulfate. The solvent was removed under reduced pressure, and the resulting product was purified on a column of silica gel (Hex:EtOAc) to give the title compound as a yellow liquid (5.4 g, 90%). $^1$H NMR (CDCl$_3$): δ 1.09 (d, 6H, 2×CH$_3$), 1.95 (m, 2H, CH$_2$), 2.31 (t, 2H, CH$_2$), 2.54 (t, 2H, CH$_2$), 3.2 (m, 1H, CH), 3.78 (s, 3H, OCH$_3$).

Example 5

6-Hydroxymethylene-2-isopropyl-3-methoxy-cyclohex-2-enone

To a suspension of sodium hydride (3.6 g, 60% suspension, 90 mmol) in benzene (100 mL), a mixture of ethyl formate (12.5 g) and 2-isopropyl-3-methoxy-cyclohex-2-enone (5g, 29.7 mmol) in benzene was added dropwise at 5° C. The reaction mixture was stirred at ice temperature for 1 hour, and at room temperature for 18 hours. The reaction mixture was cooled in an ice bath, and 10% sodium hydrogen phosphate solution (200 mL) was added dropwise. The organic layer was separated, and the aqueous layer was extracted with ethyl acetate (2×50 mL). The combined organic layers were washed with brine and dried over anhydrous sodium sulfate. The solvent was removed in vacuo, and the resulting product was purified on a column of silica gel (Hex:EtOAc) to give the title compound as a thick viscous liquid (3.5 g, 60%). $^1$H NMR (CDCl$_3$): δ 1.15 (d, 6H, 2×CH$_3$), 2.35–2.6 (m, 4H, 2×CH$_2$), 3.15 (m, 1H, CH), 3.8 (s, 3H, OCH$_3$), 7.17 (d, 1H, =CHOH).

Example 6

8-Isopropyl-7-methoxy-quinazolin-2-ylamine

A mixture of 6-hydroxymethylene-2-isopropyl-3-methoxy-cyclohex-2-enone (3.5 g) and guanidine carbonate (7 g) in DMF (40 mL) was heated at 150° C. for 4 hours. The solvent was removed under reduced pressure, then ice-cold water was added to the residue. The product was extracted with ethyl acetate (3×50 mL). The combined organic layers were washed with water, then brine, and dried over anhydrous sodium sulfate. Solvent was removed under reduced pressure to give a crude mixture of dihydroquinazolines (4 g). The dihydroquinazolines were aromatized to the title compound by heating in nitrobenzene (70 mL) at 150° C. in the presence of 10% Pd-C (400 mg) for 3 days. The catalyst was removed by filtration, then the filtrate was concentrated, and the resulting product was purified on a column of silica gel (Hex:EtOAc) to give the title compound as an off-white solid (2.1 g, 54.2%). mp 112–113° C.; $^1$H NMR (CDCl$_3$): δ 1.38 (d, 6H, 2×CH$_3$), 3.95 (s, 3H, OCH$_3$), 4.24 (m, 1H, CH), 5.0 (br s, 2H, NH$_2$), 7.02 (d, 1H, Ar-H, J=9 Hz), 7.55 (d, 1H, Ar-H, J=9 Hz), 8.87 (s, 1H, Ar-H); MS m/z 218.05, C$_{12}$H$_{15}$N$_3$O (M$^+$+1).

Example 7

8-Isopropyl-7-methoxy-1H-quinazolin-2-one

To a solution of 2-amino-7-methoxy-8-(2-propyl) quinazoline (1.3 g) in tetrafluoroboric acid (50 mL), sodium nitrite solution (2.6 g in 10 mL of water) was added dropwise at 0° C. The reaction mixture was stirred at 0° C. for 1 hour and at room temperature for 18 hours. The reaction mixture was cooled in an ice bath and neutralized with 30% ammonia solution. The product was extracted with ethyl acetate (3×50 mL), combined organic extract was washed with brine and dried over anhydrous sodium sulfate. The solvent was removed under reduced pressure to give the title compound as an off-white solid (1.2 g, 92.3%). mp 188–190° C. (decom); $^1$H NMR (CDCl$_3$): δ 1.32 (d, 6H, 2×CH$_3$), 3.44 (m, 1H, CH), 3.97 (s, 3H, OCH$_3$), 6.88 (d, 1H, Ar-H, J=8.8 Hz), 7.59 (d, 1H, Ar-H, 8.8 Hz), 9.0 (s, 1H, Ar-H), 9.1 (brs, 1H, NH).

Example 8

2-Chloro-8-isopropyl-7-methoxy-quinazoline

7-Methoxy-8-(2-propyl)quinazol-2(1H)-one (1.2 g) was dissolved in 25 mL of phosphorus oxychloride, and the resulting reaction mixture was heated at 110° C. for 2 hours. Excess POCl$_3$ was removed under reduced pressure. To the residue ice-cold water was added, and the product was extracted with ethyl acetate (3×50 mL). The combined organic extract was washed with brine, dried over anhydrous sodium sulfate, and concentrated to give the title compound. This was purified on a column of silica gel (Hexane:Ethyl acetate), off-white solid (780 mg, 60%) mp 135–137° C.; $^1$H NMR (CDCl$_3$): δ 1.41 (d, 6H, 2×CH$_3$), 4.02 (s, 3H, OCH$_3$), 4.33 (m, 1H, CH), 7.38 (d, 1H, Ar-H, J=9 Hz), 7.8 (d, 1H, Ar-H, J=9 Hz), 9.1 (s, 1H, Ar-H).

Example 9

(8-Isopropyl-7-methoxy-quinazolin-2-yl)-phenyl-amine

A mixture of 2-chloro-7-methoxy-8-(2-propyl)quinazoline (100 mg, 0.42 mmol) and aniline (120 mg, 1.29 mmol) in acetonitrile (3 mL), was heated at 80° C. for 18 hours in a sealed tube. The solvent was removed under reduced pressure, to the residue 5% sodium carbonate solution was added. The product was extracted with ethyl acetate (3×25 mL). The combined organic extract was washed with brine, dried (Na$_2$SO$_4$), and concentrated. The product was purified on a column of silica gel to give the title compound as an off-white solid (95 mg, 76.3%), mp 172–173° C.; $^1$H NMR (CDCl$_3$): δ 1.46 (d, 6H, 2×CH$_3$), 3.97 (s, 3H, OCH$_3$), 4.33 (m, 1H, CH), 7.0–7.1 (m, 2H, Ar-H), 7.38 (t, 2H, Ar-H, 7.58 (d, 1H, Ar-H), 7.85 m, 2H, Ar-H), 8.93 (s, 1H, Ar-H); MS m/z C$_{18}$H$_{19}$N$_3$O 294.21 (M$^+$+1); Analysis: Calcd.; C, 73.7; H, 6.53; N, 14.32. Found: C, 73.8; H, 6.83; N, 14.59.

Example 10

6-Cyclopentyl-1,5-dimethoxy-cyclohexa-1,4-diene

To a solution of 2,5-dihydro-1,3-dimethoxybenzene (9.88 g, 70 mmol) in dry THF (150 mL) was added dropwise nBuLi solution (2.5 M, 42.4 mL) in hexane at −20° C. The orange colored reaction mixture was stirred for 0.5 hour at −20° C., then cyclopentyl bromide (20.9 g, 140 mmol) was added dropwise. The reaction mixture was stirred for 1 hour at −20° C. to 0° C. Excess nBuLi was destroyed cautiously with methanol. To the reaction mixture, 140 mL of cold water was added. The product was extracted with ethyl acetate (3×80 mL). The combined organic extract was washed with brine, dried over anhydrous sodium sulfate, and concentrated to give the title compound as light yellow liquid (14.12 g, 96.8%). $^1$H NMR: δ 1.0–2.4 (Complex, 9H), 2.7–2.94 (m, 3H), 3.52 (s, 6H, 2×OCH$_3$), 4.70 (t, 2H).

Example 11

2-Cyclopentyl-3-methoxy-cyclohex-3-enone

To a solution of 2-cyclopentyl-2,5-dihydro-1, 3dimethoxybenzene (5 g, 27 mmol) in methanol (50 mL) was added 2.5% hydrochloric acid (10 mL) dropwise at 0° C. The reaction mixture was stirred for 45 minutes and diluted with 30 mL of ice-cold water. The product was extracted with ether (3×100 mL). The combined organic extract was washed with brine and dried (Na$_2$SO$_4$). Removal of the solvent in vacuo yielded the title compound as light yellow oil (4.3 g, 94.7%).

Example 12

2-Cyclopentyl-3-methoxy-cyclohex-2-enone

To a solution of 2-cyclopentyl-3-methoxycyclohex-3-en-1-one (4.3 g) in dry THF (120 mL), sodium methoxide (1.1 g) was added in portions at room temperature. After stirring the reaction mixture at room temperature for 1.5 hours, cooled in an ice bath, and neutralized with sodium hydrogen phosphate solution. The organic layer was separated, aqueous layer was extracted with ethyl acetate (2×50 mL). The combined organic extract was washed with brine and dried over anhydrous sodium sulfate. The solvent was removed under reduced pressure, and the resulting product was purified on a column of silica gel (Hex:EtOAc) to give the title compound as yellow liquid (2.82 g, 65.5%). $^1$H NMR (CDCl$_3$): δ 1.25–1.8 (m, 8H, 4×CH$_2$), 1.96 (m, 2H, CH$_2$), 2.36 (t, 2H, CH$_2$), 2.56 (t, 2H, CH$_2$), 3.22 (m, 1H, CH), 3.79 (s, 3H, OCH$_3$).

Example 13

2-Cyclopentyl-6-hydroxymethylene-3-methoxy-cyclohex-2-enone

To a suspension of sodium hydride (2.04 g, 60% suspension, 51 mmol) in benzene (100 mL), a mixture of ethyl formate (6.7 g) and 2-cyclopentyl-3-methoxycyclohex-3-en-1-one (2.82 g, 17 mmol) in benzene was added dropwise at 5° C. The reaction mixture was stirred at ice temperature for 1 hour and 18 hours at room temperature. The reaction mixture was cooled in ice bath, and 200 mL of 10% sodium hydrogen phosphate solution was added dropwise. The organic layer was separated, and aqueous layer was extracted with ethyl acetate (2×50 mL). Combined organic extract was washed with brine and dried over anhydrous sodium sulfate. Solvent was removed in vacuo and the resulting product was purified on a column of silica gel (Hex:EtOAc) to give the title compound as a viscous liquid (2 g, 60%).

Example 14

8-Cyclopentyl-7-methoxy-quinazolin-2-ylamine

A mixture of 6-formyl-2-cyclopentyl-3-methoxycyclohex-2-en-1-one (2.0 g, 10.2 mmol) and guanidine carbonate (4.6 g) in DMF (30 mL) was heated at 150° C. for 4 hours. The solvent was removed under reduced pressure and to the residue ice-cold water was added. The product was extracted with ethyl acetate (3×50 mL). The combined organic extract was washed with water and brine and dried over anhydrous sodium sulfate. Solvent was removed under reduced pressure to give 2.0 g of crude dihydroquinazoline. The dihydroquinazoline was aromatized to the title compound by heating in nitrobenzene at 150° C. in the presence of 10% Pd-C. To a solution of dihydroquinazoline (2.0 g, 8.2 mmol) in nitrobenzene (20 mL), 200 mg of 10% Pd-C was added, and the reaction mixture was heated at 150° C. for 3 days. The Pd-C was removed by filtration. The filtrate was concentrated, and the resulting product was purified on a column of silica gel (Hex:EtOAc) to give the title compound as an off-white solid (1 g, 50% yield), mp 181–183° C.; $^1$H NMR (CDCl$_3$): δ 1.6–2.2 (complex, 8H, 4×CH$_2$), 3.9 (s, 3H, OCH$_3$), 4.27 (t, 1H, CH), 5.02 (brs, 2H, NH$_2$), 7.02 (d, 1H, Ar-H, J=9 Hz), 7.54 (d, 1H, Ar-H, J=9 Hz), 8.87 (s, 1H, Ar-H); MS m/z 244.07, C$_{14}$H$_{17}$N$_3$O (M$^+$+1).

Example 15

8-Cyclopentyl-7-methoxy-1H-quinazolin-2-one

To a solution of 2-amino-8-cyclopentyl-7-methoxyquinazoline (1.38 g,) in tetrafluoroboric acid (30 mL), sodium nitrite solution (1.16 g in 10 mL of water) was added dropwise at 0° C. The reaction mixture was stirred at 0° C. for 1 hour and at room temperature for 18 hours. The reaction mixture was cooled in a ice bath and neutralized with 30% ammonia solution. The product was extracted with ethyl acetate (3×50 mL), combined organic extract was washed with brine and dried over anhydrous sodium sulfate. The solvent was removed under reduced pressure to give the title compound as a orange solid (1.0 g, 73%). mp 201–204° C.; $^1$H NMR (CDCl$_3$): δ 1.7–2.0 (complex, 8H, 4×CH$_2$), 3.43 (m, 1H, CH), 3.96 (s, 3H, OCH$_3$), 6.89 (d, 1H, Ar-H, J=8.8 Hz), 7.59 (d, 1H, Ar-H, J=8.8 Hz), 8.92 (brs, 1H, NH), 9.03 (s, 1H, Ar-H).

Example 16

2-Chloro-8-cyclopentyl-7-methoxy-quinazoline

7-Methoxy-8-(2-propyl)quinazol-2(1H)-one (0.95 g) was dissolved in 40 mL of phosphorus oxychloride, and the resulting reaction mixture was heated at 110° C. for 4 hours. Excess POCl$_3$ was removed under reduced pressure. To the residue ice-cold water was added, and the product was extracted with ethyl acetate (3×50 mL). The combined organic extract was washed with brine, dried over anhydrous sodium sulfate, and concentrated to give the title compound. This was purified on a column of silica gel (Hexane:Ethyl acetate), beige solid, (710 mg, 69% yield), mp 250° C. (decomp); $^1$H NMR (CDCl$_3$): δ 1.7–2.0 (complex, 8H, 4×CH$_2$), 4.17 (s, 3H, OCH$_3$), 4.27 (m, 1H, CH), 7.65 (d, 1H, Ar-H, J=9 Hz), 8.30 (d, 1H, Ar-H), 9.71 (s, 1H, Ar-H).

Example 17

(8-Cyclopentyl-7-methoxy-quinazolin-2-yl)-phenyl-amine

A mixture of 2-chloro-7-methoxy-8-(2-propyl)quinazoline (200 mg, 0.76 mmol) and aniline (212 mg, 2.28 mmol) in acetonitrile (3 mL) was heated at 90° C. for 60 hours in a sealed tube. The solvent was removed under reduced pressure, to the residue 5% sodium carbonate solution was added. The product was extracted with ethyl acetate (3×40 mL). The combined organic extract was washed with brine, dried (Na$_2$SO$_4$), and concentrated. The product was purified on a column of silica gel to give the title compound as a yellow solid (90 mg, 37%), mp 187–188° C.; $^1$H NMR (CDCl$_3$) δ: 1.72–2.30 (complex, 8H, 4×CH$_2$), 3.96 (s, 3H, OCH$_3$), 4.33 (m, 1H, CH), 7.23–7.41 (m, 2H, Ar-H), 7.58 (d, 1H, Ar-H), 7.83 (d, 2H, Ar-H), 8.93 (s, 1H, Ar-H); MS: m/z 319.81, C$_{20}$H$_{21}$N$_3$O; Analysis: Calcd.: C, 75.21; H, 6.63; N, 13.16. Found: C, 75.03; H, 6.73; N, 13.05.

Example 18

General Procedure for Coupling Anilines

A mixture of 2-chloroquinazoline (0.03 mmol) and the appropriate aniline (0.09 mmol) in acetonitrile (5 mL) was heated in a sealed tube for 24 to 72 hours at 110° C. Solvent was removed under reduced pressure, and the residue was suspended in ethyl acetate and treated with 5% Na$_2$CO$_3$ solution. The organic layer was separated, and the aqueous layer was extracted with ethyl acetate (2×20 mL). The combined organic extracts were washed with brine and dried over Na$_2$SO$_4$. The product was purified by chromatography on silica gel.

Example 19

(8-Isopropyl-7-methoxy-quinazolin-2-yl)-phenyl-amine mp. 172–173° C.; $^1$H NMR (CDCl$_3$) δ 1.46 (d, 6H, 2×CH$_3$), 3.97 (s, 3H, OCH$_3$), 4.33 (m, 1H, CH), 7.0–7.1 (m, 2H, Ar-H), 7.38 (t, 2H, Ar-H, 7.58 (d, 1H, Ar-H), 7.85 m, 2H, Ar-H), 8.93 (s, 1H, Ar-H); MS: m/z $C_{18}H_{19}N_3O$ 294.21 ($M^+$+1); Analysis: Calcd.: C, 73.7; H, 6.53; N, 14.32. Found: C, 73.8; H, 6.83; N, 14.59.

Example 20

1-{4-[4-(8-Cyclopentyl-7-methoxy-quinazolin-2-ylamino)-phenyl]-piperazin-1-yl}-ethanone Yellow solid, yield 83%, mp 247–249° C.; $^1$H NMR (CDCl$_3$) δ: 1.6–2.3 (complex, 8H, 4×CH$_2$), 2.18 (s, 3H, COCH$_3$), 3.13 (m, 4H), 3.63 (m, 2H), 3.78 (m, 2H), 3.96 (s, 3H, OCH$_3$), 4.30 (m, 1H, CH), 6.96 (d, 2H, Ar-H, J=9 Hz), 7.05 (d, 1H, Ar-H, J=8.8 Hz), 7.11 (s, 1H, NH), 7.56 (d, 1H, Ar-H, J=8.8 Hz), 7.72 (d, 2H, Ar-H, J=9 Hz), 8.90 (s, 1H, Ar-H); MS (ES): m/z 446.29, $C_{26}H_{31}N_5O_2$, (MH$^+$). Analysis: Calcd.: C, 70.09; H, 7.01; N, 15.72. Found: C, 69.38; H, 7.43; N, 15.06.

Example 21

(8-Isopropyl-7-methoxy-quinazolin-2-yl)-(4-piperidin-1-yl-phenyl)-amine

Yellow solid, Yield 54.5%, mp 166–167° C.; $^1$H NMR (CDCl$_3$): δ 1.44 (d, 6H, 2×CH$_3$), 1.6 (m, 2H, CH$_2$), 1.74 (m, 4H, 2×CH$_2$), 3.13 (t, 4H, 2×CH$_2$), 3.96 (s, 3H, OCH3) 4.30 (m, 1H, CH), 6.9–7.1 (2d and s merged, 3 Ar-H, NH), 7.54 (d, 1H, Ar-H), 7.7 (d, 2H, Ar-H), 8.88 (s, 1H, Ar-H); MS (ES): m/z 376.97, $C_{23}H_{28}N_4O$ (M$^+$); Analysis: Calcd.: C, 73.37; H, 7.5; N, 14.88. Found: C, 73.18; H, 7.69; N, 14.89.

Example 22

(8-Isopropyl-7-methoxy-quinazolin-2-yl)-(4-pyrrolidin-1-yl-phenyl)-amine

Orange solid, 64.7%, mp 188–190° C.; $^1$H NMR (CDCl$_3$): δ 1.43 (d, 6H, 2×CH$_3$), 2.01 (m, 4H, 2×CH$_2$), 3.30 (t, 4H, 2×CH$_2$), 3.95 (s, 3H, OCH$_3$), 4.29 (m, 1H CH), 6.61 (d, 2H, Ar-H, J=8.9 Hz), 6.9–7.1 (d and s merged, 2H, Ar-H, NH), 7.52 (d, 1H, Ar-H, J=8.9 Hz), 7.63 (d, 2H, Ar-H, J=8.9 Hz), 8.85 (s, 1H, Ar-H); MS (ES): m/z 363.02, $C_{22}H_{26}N_4O$ (M$^+$+1); Analysis: Calcd., C, 72.90; H, 7.23; N, 15.46. Found: C, 73.35; H, 7.67; N, 14.74.

Example 23

(8-Cyclopentyl-7-methoxy-quinazolin-2-yl)-(4-piperidin-1-yl-phenyl)-amine

Yellow solid, 28%, mp 212–214° C.; $^1$H NMR (CDCl$_3$): δ 1.55–2.28 (complex, 14H, 7×CH$_2$), 3.08–3.14 (m, 4H, 2×CH$_2$), 3.95 (s, 3H, OCH$_3$), 4.29 (m, 1H, CH), 6.94–7.08 (complex, 4H, 3Ar-H, NH), 7.52–7.57 (m, 1H, Ar-H), 7.65–7.72 (m, 2H, Ar-H), 8.88 (s, 1H, Ar-H); MS (ES): m/z 403.17, $C_{25}H_{30}N_4O$ (M$^+$+1); Analysis: Calcd.: C, 74.60; H, 7.51; N, 13.92. Found: C, 74.83; H, 7.57; N, 13.82.

Example 24

(8-Cyclopentyl-7-methoxy-quinazolin-2-yl)-(4-pyrrolidin-1-yl-phenyl)-amine

Yellow solid, yield 42.7%, mp 240–242° C.; $^1$H NMR (CDCl$_3$): δ 1.68–2.29 (complex, 12H, 6×CH$_2$), 3.30 (m, 4H, 2×CH$_2$), 3.94 (s, 3H, OCH$_3$), 4.28 (m, 1H, CH), 6.59 (d, 2H, Ar-H, J=8.9 Hz), 6.95 (s, 1H, NH), 7.0 (d, 1H, Ar-H, J=8.9 Hz,), 7.52 (d, 1H, Ar-H, J=8.9 Hz), 7.60 (d, 2H, Ar-H, J=8.9 Hz), 8.86 (s, 1H, Ar-H); MS (ES): m/z 388.98, $C_{24}H_{28}N_4O$ (M$^+$); Analysis: Calcd.: C, 74.20; H, 7.26; N, 14.42. Found: C, 73.94; H, 7.34; N, 14.36.

Example 25

4-[4-(8-Isopropyl-7-methoxy-quinazolin-2-ylamino)-phenyl]-piperazine-1-carboxylic Acid Tert-butyl Ester Yellow solid, yield 64.4%, mp 173–175° C.; $^1$H NMR (CDCl$_3$): δ 1.44 (d, 6H, 2×CH$_3$), 1.49 (s, 9H, 3×CH$_3$), 3.1 (t, 4H, 2×CH$_2$), 3.6 (t, 4H, 2×CH$_2$), 3.96 (s, 3H, OCH$_3$), 4.3 (m, 1H, CH), 6.98 (d, 2H, Ar-H), 7.04 (d, 1H, Ar-H), 7.13 (s, 1H, NH), 7.56 (d, 1H, Ar-H), 7.74 (d, 2H, Ar-H), 8.89 (s, 1H, Ar-H); MS (ES): m/z 478.11, $C_{27}H_{35}N_5O_3$ (M$^+$+1); Analysis: Calcd. C, 67.9; H, 7.39; N, 14.66. Found: C, 68.06; H, 7.61; N, 14.16.

Example 26

4-[4-(8-Cyclopentyl-7-methoxy-quinazolin-2-ylamino)-phenyl]-piperazine-1-carboxylic Acid Tert-butyl Ester Yellow solid, yield 54%, mp 183–184° C.; $^1$H NMR (CDCl$_3$): δ 1.49 (s, 9H, 3×CH$_3$), 1.68–2.29 (complex, 8H, 4×CH$_2$), 3.10 (t, 4H, 2×CH$_2$), 3.61 (t, 4H, 2×CH$_2$), 3.96 (s, 3H, OCH$_3$), 4.29 (m, 1H, CH), 6.96 (d, 2H, Ar-H, J=8.9 Hz), 7.04 (d, 1H, J=8.9 Hz), 7.09 (s, 1H, NH), 7.56 (d, 1H, Ar-H, J=8.9 Hz), 7.71 (d, 2H, Ar-H, J=8.9 Hz), 8.89 (s, 1H, Ar-H); MS (ES): m/z 504.35, $C_{29}H_{37}N_5O_3$ (M$^+$+1); Analysis: Calcd.: C, 69.16; H, 7.4; N, 13.91. Found: C, 68.84; H, 7.73; N, 13.58.

Example 27

(8-Cyclopentyl-7-methoxy-quinazolin-2-yl)-(4-piperazin-1-yl-phenyl)-amine

Yellow solid, yield 77%, mp 218–219° C.; $^1$H NMR (CDCl$_3$): δ 1.68–2.29 (complex, 8H, 4×CH$_2$), 3.11 (m, 8H, 4×CH$_2$), 3.96 (s, 3H, OCH$_3$), 4.30 (m, 1H, CH), 6.97 (d, 2H, Ar-H, J=8.9 Hz), 7.04 (d, 1H, J=8.8 Hz), 7.06 (s, 1H, NH), 7.55 (d, 1H, Ar-04.12, $C_{24}H_{29}N_5O$ (M$^+$+1); Analysis: Calcd.: C, 71.44; H, 7.24; N, 17.36. Found: C, 70.33; H, 7.86; N, 16.73.

Example 28

1-{4-[4-(8-Isopropyl-7-methoxy-quinazolin-2-ylamino)-phenyl]-piperazine-1-yl}-ethanone Light yellow solid, yield 79%, mp 197–198° C.; $^1$H NMR (CDCl$_3$): δ 1.44 (d, 6H, 2×CH$_3$), 2.16 (s, 3H, COCH$_3$), 3.15 (m, 4H), 3.65 (m, 2H), 3.80 (m, 2H), 3.97 (s, 3H, OCH$_3$), 4.30 (m, 1H, CH), 6.98 (d, 2H, Ar-H), 7.04 (d, 1H, Ar-H), 7.13 (s, 1H, NH), 7.56 (d, 1H, Ar-H), 7.75 (d, 2H, Ar-H), 8.89 (s, 1H, Ar-H); MS (ES): m/z 420.0 $C_{24}H_{20}N_5O_2$ (M$^+$+1); Analysis: Calcd.: C, 68.71; H, 6.97; N, 16.69. Found: C, 69.07; H, 7.42; N, 16.24.

Example 29

8-Isopropyl-2-phenylamino-quinazolin-7-ol

A mixture of 1 (150 mg, 0.51 mmol) and sodium thioethoxide (214 mg, 2.55 mmol) in dimethylformamide (5 mL) was heated at 150° C. for 5 hours. The solvent was removed under reduced pressure. To the residue, ice-cold water (30 mL) was added, and the mixture was acidified with acetic acid (0.5 mL). The product was extracted with ethyl acetate (3×30 mL). The combined organic extracts were washed with brine, dried over anhydrous sodium sulfate, and concentrated. The product was purified on a column of silica gel (EtOAc:MeOH) to give a light yellow solid, yield 70%, mp 103–104° C.; $^1$H NMR (CDCl$_3$): δ 1.52 (d, 6H, 2×CH$_3$), 4.30 (m, 1H, CH), 5.7 brs, 1H, OH), 6.83 (d, 1H, Ar-H, J=8.7 Hz), 7.06 (m, 1H, Ar-H), 7.3–7.5 (s and m merged, 3H, 2 Ar-H, NH), 7.49 (d, 1H, Ar-H, 8.7 Hz), 7.83 (m, 2H, Ar-H), 8.89 (s, 1H, Ar-H); MS (ES): m/z 279.37, C$_{17}$H$_{17}$N$_3$O (M$^+$). Analysis: Calcd.: C, 73.10; H, 6.13; N, 15.04. Found: C, 73.34; H, 6.37; N, 14.72.

Example 30

General Procedure for Deprotection of an N-Boc Group

To a solution of N-Boc-protected compound (0.2 mmol) in dichloromethane (3 mL) was added trifluoroacetic acid dropwise. The reaction mixture was stirred at room temperature for 3 hours. The solvent was removed under reduced pressure, and to the residue was added ice-cold water (30 mL). This mixture was basified with 5% Na$_2$CO$_3$ solution, then the product was extracted with chloroform (3×30 mL). The combined organic extracts were washed with brine and dried over anhydrous sodium sulfate. The solvent was removed under reduced pressure, and the product was purified on a column of florisil (EtOAc:MeOH).

Example 31

(8-Isopropyl-7-methoxy-quinazolin-2-yl)-(4-piperaziny-1-yl-phenyl)-amine

Amorphous solid, yield 84.4%. $^1$H NMR (CDCl$_3$): δ 1.44 (d, 6H, 2×CH$_3$), 3.0–3.2 (m, 8H, 4×CH$_2$), 3.96 (s, 3H, OCH$_3$), 4.3 (m, 1H, CH), 6.9–7.1 (2d merged, 3H, Ar-H), 7.2 (s, 1H, NH), 7.55 (d, 1H, Ar-H), 7.73 (d, 2H, Ar-H), 8.88 (s, 1H, Ar-H); MS (ES): m/z 378.15, C$_{22}$H$_{27}$N$_5$O (M$^+$+1).

Example 32

2-Amino-1-{4-[4-(8-Isopropyl-7-methoxy-quinazolin-2-ylamino)-phenyl]-piperazin-1-yl}-ethanone Yellow solid, yield 85%, mp 183–185° C.; $^1$H NMR (CDCl$_3$): δ 1.44 (d, 6H, 2×CH$_3$), 3.15 (m, 4H), 3.52 (s, 2H), 3.55 (m, 2H, CH$_2$), 3.83 (m, 2H), 3.97 (s, 3H, OCH$_3$), 4.30 (m, 1H, CH), 6.98 (d, 2H, Ar-H, 8.9 Hz), 7.05 (d, 1H, Ar-H, 8.9 Hz), 7.14 (s, 1H, NH), 7.56 (d, 1H, Ar-H, J=8.9 Hz), 7.76 (d, 2H, Ar-H, J=8.9 Hz), 8.89 (s, 1H, Ar-H); MS (ES): m/z 434.66 C$_{24}$H$_{30}$N$_6$O2 (M$^1$).

Example 33

1-{4-[4-(8-Isopropyl-7-methoxy-quinazolin-2-ylamino)-phenyl]-piperazin-1-yl}-ethanone Light yellow solid, yield 79%, mp 197–198° C.; $^1$H NMR (CDCl$_3$) δ: 1.44 (d, 6H, 2×CH$_3$), 2.16 (s, 3H, COCH$_3$), 3.15 (m, 4H), 3.65 (m, 2H), 3.80 (m, 2H), 3.97 (s, 3H, OCH$_3$), 4.30 (m, 1H, CH), 6.98 (d, 2H, Ar-H), 7.04 (d, 1H, Ar-H), 7.13 (s, 1H, NH), 7.56 (d, 1H, Ar-H), 7.75 (d, 2H, Ar-H), 8.89 (s, 1H, Ar-H). MS (ES): m/z 420.0 C$_{24}$H$_{29}$N$_5$O$_2$ (M$^+$+1); Analysis: Calcd. C, 68.71; H, 6.97; N, 16.69. Found: C, 69.07; H, 7.42; N, 16.24.

Example 34

(8-Isopropyl-7-methoxy-quinazolin-2-yl)-(4-piperazin-1-yl-phenyl)-amine

Amorphous solid, Yield 84.4%. $^1$H NMR (CDCl$_3$) δ: 1.44 (d, 6H, 2×CH$_3$), 3.0–3.2 (m, 8H, 4×CH$_2$), 3.96 (s, 3H, OCH$_3$), 4.3 (m, 1H, CH), 6.9–7.1 (2d merged, 3H, Ar-H), 7.2 (s, 1H, NH), 7.55 (d, 1H, Ar-H), 7.73 (d, 2H, Ar-H), 8.88 (s, 1H, Ar-H). MS (ES): m/z 378.15, C$_{22}$H$_{27}$N$_5$O (M$^+$+1).

Example 35

2-Amino-1-{4-[4-(8-Isopropyl-7-methoxy-quinazolin-2-ylamino)-phenyl]-piperazin-1-yl}-ethanone Yellow solid, yield 85%, mp 183–185° C.; $^1$H NMR (CDCl$_3$) δ: 1.44 (d, 6H, 2×CH$_3$), 3.15 (m, 4H), 3.52 (s, 2H), 3.55 (m, 2H, CH$_2$), 3.83 (m, 2H), 3.97 (s, 3H, OCH$_3$), 4.30 (m, 1H, CH), 6.98 (d, 2H, Ar-H, 8.9 Hz), 7.05 (d, 1H, Ar-H, 8.9 Hz), 7.14 (s, 1H, NH), 7.56 (d, 1H, Ar-H, J=8.9 Hz), 7.76 (d, 2H, Ar-H, J=8.9 Hz), 8.89 (s, 1H, Ar-H). MS (ES): m/z 434.66 C$_{24}$H$_{30}$N$_6$O2 (M$^1$).

Example 36

(8-Isopropyl-7-methoxy-quinazolin-2-yl)-(4'-methoxy-biphenyl-4-yl)-amine

Solid, yield 69%, mp 198–199° C.; $^1$H NMR (CDCl$_3$) δ: 1.45 (d, 6H, 2×CH$_3$), 3.2–3.4 (m, 8H, 4×CH$_2$), 3.78 (s, 3H, OCH$_3$), 3.96 (s, 3H, OCH$_3$), 4.31 (m, 1H, CH), 6.8–7.2 (complex, 8H, 7 Ar-H, NH), 7.56 (d, 1H, Ar-H), 7.75 (d, 2H, Ar-H), 8.89 (s, 1H, Ar-H). MS (ES): m/z 484.22 C$_{29}$H$_{33}$N$_5$O$_2$ (M$^+$+1). Analysis: Calcd. C, 72.02; H, 6.88; N, 14.48. Found: C, 71.58; H, 7.30; N, 14.29.

Example 37

[4-(3-Amino-pyrrolidin-1-yl)-phenyl]-(8-isopropyl-7-methoxy-quinazolin-2-yl)-amine Yellow solid, yield 82.3%, mp 125–127° C., $^1$H NMR (CDCl$_3$) δ: 1.43 (d, 6H, 2×CH$_3$), 1.84 (m, 1H), 2.3 (m, 1H), 3.08 (m, 1H), 3.3–3.6 (complex, 3H), 3.76 (m, 1H), 3.95 (s, 3H, OCH$_3$), 4.30 (s, 1H), 6.59 (d, 2H, Ar-H, J=8.7 Hz), 6.99 (d, 1H, Ar-H, J=8.8 Hz), 7.02 (s, 1H, NH), 7.52 (d, 1H, Ar-H, J=8.8 Hz), 7.64 (d, 2H, Ar-H, J=8.7 Hz), 8.86 (s, 1H, Ar-H). MS (ES): m/z 378.15 (MH$^+$) C$_{22}$H$_{27}$N$_5$O.

Example 38

(3-Fluoro-4-morpholin-4-yl-phenyl)-(8-isopropyl-7-methoxy-quinazolin-2-yl)-amine Yellow solid, yield 65.7%, mp 202–203° C.; $^1$H NMR (DMSO-d$_6$) δ: 1.41 (d, 6H, 2×CH$_3$), 2.96 (t, 4H, 2×CH$_2$), 3.74 (t, 4H, 2×CH$_2$), 3.95 (s, 3H, OCH$_3$), 4.25 (m, 1H, CH), 7.01 (m, 1H, Ar-H), 7.24 (d, 1H, Ar-H, J=8.9 Hz), 7.55 (m, 1H, Ar-H), 7.78 (d, 1H, Ar-H, J=8.9 Hz), 8.04 (m, 1H, Ar-H), 9.12 (s, 1H, Ar-H), 9.79 (s, 1H, NH). MS(ES), 397.35 (MH$^+$), C$_{22}$H$_{25}$FN$_4$O$_2$. Analysis: Calcd.: C, 66.65; H, 6.36; N, 14.13. Found: C, 66.76; H, 6.34; N, 13.96.

Example 39

(8-Isopropyl-7-methoxy-quinazolin-2-yl)-(4-morpholin-4-yl-phenyl)-amine

Yellow solid, yield 81.8%, mp 187–189° C.; $^1$H NMR (CDCl$_3$) δ: 1.44 (d, 6H, 2×CH$_3$), 3.15 (t, 4H, 2×CH$_2$), 3.89 (t, 4H, 2×CH$_2$), 3.96 (s, 3H, OCH$_3$), 4.31 (m, 1H, CH), 6.97 (d, 2H, Ar-H, J=8.9 Hz), 7.04 (d, 1H, Ar-H, J=8.9 Hz), 7.12 (s, 1H, NH), 7.56 (d, 1H, Ar-H, J=8.9 Hz), 7.75 (d, 2H, Ar-H, J=8.9 Hz), 8.89 (s, 1H, Ar-H). MS (ES): m/z 379.18 (MH$^+$), C$_{22}$H$_{26}$N$_4$O$_2$. Analysis: Calcd.: C, 69.82; H, 6.92; N, 14.80. Found: C, 69.95; H, 7.06; N, 14.59.

Example 40

2-Amino-1-{4-[4-(8-cyclopentyl-7-methoxy-quinazolin-2-ylamino)-phenyl]-piperazin-1-yl}-ethanone Yellow solid, yield 60%, mp 202° C.; $^1$H NMR (CDCl$_3$) δ: 1.6–2.3 (complex, 8H, 4×CH$_2$), 3.1 (t, 4H, 2×CH$_2$), 3.52 (s, 2H, CH$_2$), 3.56 (m, 2H), 3.83 (m, 2H), 3.96 (s, 3H, OCH$_3$), 4.3 (m, 1H, CH), 6.96 (d, 2H, Ar-H, J=9 Hz), 7.05 (d, 1H, Ar-H, 8.9 Hz), 7.1 (s, 1H, NH), 7.57 (d, 1H, Ar-H, J=8.9 Hz), 7.72 (d, 2H, Ar-H, J=9 Hz), 8.9 (s, 1H, Ar-H). MS (ES): m/z 461.19 (MH$^+$), C$_{26}$H$_{32}$N$_6$O$_2$.

Example 41

[4-(3-Amino-pyrrolidin-1-yl)-phenyl]-(8-cyclopentyl-7-methoxy-quinazolin-2-yl)-amine Yellow solid, yield 83%, mp 220–221° C.; $^1$H NMR (CDCl$_3$) δ: 1.6–2.4 (complex, 10H), 3.04 (m, 1H), 3.3–3.6 (m, 3H), 3.7 (m, 1H), 3.95 (s, 3H, OCH$_3$), 4.30 (m, 1H, CH), 6.58 (d, 2H, Ar-H, J=8.9 Hz), 6.98 (s, 1H, NH), 7.0 (d, 1H, Ar-H, J=8.8 Hz), 7.53 (d, 1H, Ar-H, J=8.8 Hz), 7.61 (d, 2H, Ar-H, J=8.9 Hz), 8.86 (s, 1H, Ar-H). MS (ES): m/z 404.22 (MH$^+$) C$_{24}$H$_{29}$N$_5$O. Analysis: Calcd.: C, 71.44; H, 7.24; N, 17.36. Found: C, 70.75; H, 7.44; N, 17.1.

Example 42

2-Amino-1-{4-[4-(8-cyclopentyl-7-methoxy-quinazolin-2-ylamino)-phenyl]-piperazin-1-yl}-4-methyl-pentan-1-one Yellow solid, yield 77%, mp 130–132° C.; $^1$H NMR (CDCl$_3$) δ: 0.97 (m, 6H, 2×CH$_3$), 1.39 (m, 2H), 1.6–2.1 (m, 7H), 2.2 (m, 2H), 3.16 (m, 4H), 3.64 (m, 2H), 3.8 (m, 3H), 3.81 (s, 3H, OCH$_3$), 4.3 (m, 1H, CH), 6.96 (d, 2H, Ar-H, J=8.9 Hz), 7.05 (d, 1H, Ar-H, J=8.8 Hz), 7.1 (s, 1H, NH), 7.57 (d, 1H, Ar-H, J=8.8 Hz), 7.72 (d, 2H, Ar-H, J=8.9 Hz), 8.9 (s, 1H, Ar-H). MS (ES): m/z 517.28 (MH$^+$) C$_{30}$H$_{40}$N$_6$O$_2$. Analysis: Calcd.: C, 69.14; H, 7.8; N, 16.27. Found: C, 69.08; H, 8.22; N, 15.96.

Example 43

(8-Cyclopentyl-7-methoxy-quinazolin-2-yl)-(3-fluoro-4-morpholin-4-yl-phenyl)-amine Yellow solid, yield 50%, mp 252–253° C.; $^1$H NMR (DMSO-d$_6$) δ: 1.6–2.2 (complex, 8H, 4×CH$_2$), 2.95 (t, 4H, 2×CH$_2$), 3.74 (t, 4H, 2×CH$_2$), 3.95 (s, 3H, OCH$_3$), 4.24 (m, 1H, CH), 7.05 (m, 1H, Ar-H), 7.2 (d, 1H, Ar-H, J=8.9 Hz), 7.44 (m, 1H, Ar-H), 7.78 (d, 1H, Ar-H, J=8.9 Hz), 8.07 (m, 1H, Ar-H), 9.12 (s, 1H, Ar-H), 9.78 (s, 1H, NH). MS (ES): m/z 423.19 (MH$^+$) C$_{24}$H$_{27}$FN$_4$O$_2$.

Example 44

(8-Cyclopentyl-7-methoxy-quinazolin-2-yl)-(4-morpholin-4-yl-phenyl)-amine

Yellow solid, yield 85%, mp 243–244° C.; $^1$H NMR (DMSO-d$_6$) δ: 1.6–2.3 (m, 8H, 4×CH$_2$), 3.05 (t, 4H, 2×CH$_2$), 3.75 (t, 4H, 2×CH$_2$), 3.93 (s, 3H, OCH$_3$), 4.24 (m, 1H, CH), 6.91 (d, 2H, Ar-H, J=9 Hz), 7.19 (d, 1H, Ar-H, J=8.9 Hz), 7.7–7.9 (2d merged, 3H, Ar-H), 9.06 (s, 1H, Ar-H), 9.47 (s, 1H, NH). MS (ES): m/z 405.2 (MH$^+$), C$_{24}$H$_{28}$N$_4$O$_2$.

Example 45

{1-[4-(8-Cyclopentyl-7-methoxy-quinazolin-2-ylamino)-phenyl]-pyrrolidin-3-yl}-carbamic Acid Tert-butyl Ester Yellow solid, yield 65%, mp 157° C. (decomp); $^1$H NMR (CDCl$_3$) δ: 1.57 (s, 9H, 3×CH$_3$), 1.6–2.4 (complex, 10H), 3.1–3.65 (m, 4H), 3.96 (s, 3H, OCH$_3$), 4.2–4.4 (m, 2H), 4.75 (s, 1H, CONH), 6.6 (d, 2H, Ar-H, J=8.9 Hz), 7.06 (s, 1H, NH), 7.08 (d, 1H, Ar-H, J=8.9 Hz), 7.54 (d, 1H, Ar-H, J=8.9 Hz), 7.63 (d, 2H, Ar-H, J=8.9 Hz), 8.88 (s, 1H, Ar-H). MS (ES): m/z 504.24 (MH$^+$), C$_{29}$H$_{37}$N$_5$O$_3$.

Example 46

(4-Fluoro-3-methyl-phenyl)-(8-isopropyl-7-methoxy-quinazolin-2-yl)-amine

Off-white solid, yield 80%, mp 169–171° C.; $^1$H NMR (CDCl$_3$) δ: 1.46 (d, 6H, 2×CH$_3$), 2.33 (d, 3H, Ar-CH$_3$, J=1.7 Hz), 3.97 (s, 3H, OCH$_3$), 4.3 (m, 1H, CH), 6.99 (m, 1H, Ar-H), 7.06 (d, 1H, Ar-H, J=8.9 Hz), 7.18 s, 1H, NH), 7.4 (m, 1H, Ar-H), 7.58 (d, 1H, Ar-H, J=8.9 Hz), 7.90 (m, 1H, Ar-H), 8.91 (s, 1H, Ar-H). MS (ES): m/z 326.24 (MH$^+$). Analysis: Calcd for C$_{19}$H$_{20}$FN$_3$O.⅓H$_2$O; C, 68.86; H, 6.29; N, 12.68. Found: C, 69.21; H, 6.26; N, 12.59.

Example 47

(8-Isopropyl-7-methoxy-quinazolin-2-yl)-(4-piperidin-1-yl-phenyl)-amine

Yellow solid, yield 72%, mp 160–161° C.; $^1$H NMR (CDCl$_3$) δ: 1.46 (d, 6H, 2×CH$_3$), 1.6 (m, 2H, CH2), 1.77 (m, 4H, 2×CH$_2$), 3.0 (t, 4H, 2×CH$_2$), 3.97 (s, 3H, OCH$_3$), 4.31

(m, 1H, CH), 6.96 (m, 1H, Ar-H), 7.06 (d, 1H, Ar-H, J=8.8 Hz), 7.17 (s, 1H, NH), 7.25 (m, 1H, Ar-H), 7.58 (d, 1H, Ar-H, J=8.8 Hz), 7.93 (m, 1H, Ar-H), 8.9 (s, 1H, Ar-H). MS (ES): m/z 395.48 (MH$^+$), $C_{23}H_{27}FN_4O$. Analysis: Calcd.: C, 70.03; H, 6.9; N, 14.2. Found: C, 69.44; H, 7.01; N, 14.06.

Example 48

(8-Cyclopentyl-7-methoxy-quinazolin-2-yl)-(4-fluoro-3-methyl-phenyl)-amine

Off-white solid, yield 56%, mp 208–209° C.; $^1$H NMR (CDCl$_3$) δ: 1.6–2.2 (complex, 8H, 4×CH$_2$), 2.32 (d, 3H, CH$_3$, J=1.8 Hz), 3.97 (s, 3H, OCH$_3$), 4.36 (m, 1H, CH), 6.98 (m, 1H, Ar-H), 7.07 (d, 1H, Ar-H, J=8.9 Hz), 7.13 (s, 1H, NH), 7.44 (m, 1H, Ar-H), 7.58 (d, 1H, Ar-H, J=8.9 Hz), 7.82 (m, 1H, Ar-H), 8.91 (s, 1H, Ar-H). MS (ES): m/z 352.29 (MH$^+$). $C_{21}H_{22}FN_3O$. Analysis: Calcd. for $C_{21}H_{22}FN_3O\cdot½ H_2O$; C, 69.98; H, 6.43; N, 11.66. Found: C, 69.62; H, 6.09; N, 11.51.

Example 49

(8-Cyclopentyl-7-methoxy-quinazolin-2-yl)-(3-Fluoro-4-piperidin-1-yl-phenyl)-amine Yellow solid, yield 56%, mp 200–201° C.; $^1$H NMR (CDCl$_3$) δ: 1.4–2.3 (complex, 14H, 7×CH$_2$), 3.0 (t, 4H, 2×CH$_2$), 3.96 (s, 3H, OCH$_3$), 4.32 (m, 1H, CH), 6.95 (m, 1H, Ar-H), 7.06 (d, 1H, Ar-H, J=8.8 Hz), 7.16 (m, 1H, Ar-H), 7.19 (s, 1H, NH), 7.57 (d, 1H, Ar-H, J=8.8 Hz), 7.96 (m, 1H, Ar-H), 8.9 (s, 1H, Ar-H). MS (ES): m/z 421.20 (MH$^+$). $C_{25}H_{29}FN_4O$. Analysis: Calcd. For $C_{25}H_{29}FN_4O\cdot½ H_2O$; C, 69.91; H, 7.04; N, 13.04. Found: C, 69.67; H, 6.85; N, 12.79.

Example 50

(8-Cyclopentyl-7-methoxy-quinazolin-2-yl)-(3-fluoro-4-piperazin-1-yl-phenyl)-amine Yellow solid, yield 82%, mp 228–229° C.; $^1$H NMR (CDCl$_3$) δ: 1.7–2.3 (complex, 8H, 4×CH$_2$), 3.06 (s, 8H, 4×CH$_2$), 3.97 (s, 3H, OCH$_3$), 4.3 (m, 1H, CH), 6.94 (m, 1H, Ar-H), 7.08 (d, 1H, Ar-H, J=9 Hz), 7.1–7.2 (s and m merged, 2H, NH, AR-H), 7.58 (d, 1H, Ar-H, J=9 Hz), 7.99 (m, 1H, Ar-H, 8.91 (s, 1H, Ar-H). MS (ES): m/z 422.24 (MH$^+$) $C_{24}H_{28}FN_5O$. Analysis calcd for $C_{24}H_{28}FN_5O\cdot H_2O$; C, 65.58; H, 6.88; N, 15.93. Found: C, 65.44; H, 6.2; N, 15.57.

TABLE 1

| | IC$_{50}$ values in µM | | | |
|---|---|---|---|---|
| Example Number | CdkB IC50 | Cdk2A IC50 | Cdk2E IC50 | Cdk4 IC50 |
| 19 | 1.038 | 0.253 | 1.075 | 0.125 |
| 20 | >5 | 0.050 | 0.265 | 0.002 |
| 21 | >5 | 0.410 | 3.100 | 0.052 |
| 22 | >5 | 1.597 | >5 | 0.560 |
| 23 | >5 | 0.384 | >5 | 0.011 |
| 24 | >5 | 7.690 | >5 | 1.750 |
| 25 | 10.200 | 1.622 | 10.000 | 0.063 |
| 26 | 4.200 | 0.646 | 5.000 | 0.051 |
| 27 | 0.132 | 0.028 | 0.250 | 0.001 |
| 29 | 0.813 | 0.250 | 0.550 | 0.325 |
| 33 | na | na | 0.900 | 0.025 |
| 34 | 0.506 | 0.185 | 1.200 | 0.016 |
| 35 | 0.800 | 0.191 | 1.100 | 0.010 |

TABLE 1-continued

| | IC$_{50}$ values in µM | | | |
|---|---|---|---|---|
| Example Number | CdkB IC50 | Cdk2A IC50 | Cdk2E IC50 | Cdk4 IC50 |
| 36 | na | na | >5 | 0.225 |
| 37 | 1.300 | 0.296 | 2.550 | 0.011 |
| 38 | 1.233 | 0.451 | 2.750 | na |
| 39 | 1.970 | 0.665 | 4.400 | 0.052 |
| 40 | 0.270 | 0.095 | 0.450 | 0.002 |
| 41 | 0.398 | 0.203 | 0.950 | 0.116 |
| 42 | 0.333 | 0.103 | 0.500 | na |
| 43 | >5 | 0.966 | >5 | 0.070 |
| 44 | 1.590 | 0.383 | 0.650 | 0.018 |
| 45 | >1.7 | 2.395 | 6.900 | 0.275 |
| 46 | 1.201 | 0.246 | 1.200 | 1.500 |
| 47 | 1.070 | 0.264 | 4.100 | 0.075 |
| 48 | 1.170 | 0.574 | 2.200 | 2.400 |
| 49 | >5 | na | 8.000 | 0.085 |
| 50 | 0.214 | 0.062 | 0.300 | 0.004 |

As noted above, the compounds of this invention are potent inhibitors of cyclin-dependent kinases, and accordingly, are useful in treating and preventing neurodegenerative disorders, atherosclerosis, and other cell proliferative disorders like cancer. The compounds have exhibited excellent inhibitory activity against a wide variety of cyclin-dependent kinases, all in assay systems routinely utilized to measure such activity. A typical assay, for instance, measures inhibitory activity against the cyclin D dependent kinase 4 enzyme (cdk4/D). The invention compounds of Formula I exhibited IC$_{50}$ values ranging generally from 0.011 µM to 1.75 µM. The cdk4 assay was carried out as follows.

Cyclin-Dependent Kinase 4 (cdk4) Assay

Enzyme assays for IC$_{50}$ determinations (Table 1 above) and kinetic evaluation were performed in 96 well filter plates (Millipore MADVN6550). The total volume was 0.1 mL containing a final concentration of 20 mM TRIS (tris[hydroxymethyl]aminomethane), at pH 7.4, 50 mM NaCl, 1 mM dithiothreitol, 10 mM MgCl$_2$, 25 µM ATP containing 0.25 µCi of [$^{32}$P]ATP, 20 ng of cdk4, 1 µg of retinoblastoma, and appropriate dilutions of a compound of the present invention. All components except the ATP were added to the wells, and the plate was placed on a plate mixer for 2 minutes. The reaction was started by adding [$^{32}$P]ATP and the plate was incubated at 25° C. for 15 minutes. The reaction was terminated by addition of 0.1 mL of 20% trichloroacetic acid (TCA). The plate was kept at 4° C. for at least 1 hour to allow the substrate to precipitate. The wells were then washed five times with 0.2 mL of 10% TCA and $^{32}$P incorporation was determined with a beta plate counter (Wallac Inc., Gaithersburg, Md.).

The IC$_{50}$ determinations and kinetic evaluations were performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM MgCl$_2$, 12 mM ATP containing 0.25 µCi of [$^{32}$P]ATP, 20 ng of enzyme (either cdk2/cyclinE, cdk2/A, or cdc2/cyclinB), 1 µg retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$P incorporation determined with a beta plate counter (Wallac Inc., Gaithersburg, Md.).

The $IC_{50}$ values were determined using enzyme assays performed in a total volume of 0.1 mL of a solution comprising 25 mM Hepes, pH 7.4, 5 mM $MgCL_2$, 2 mM $MnCL_2$, 50 µM sodium vanadate, 5 to 10 ng of cdk4, and 200 µM of a substrate peptide Ala-Glu-Gly-Ser-Ala-Tyr$^{472}$-Glu-Glu-Val-$NH_2$, derived from the amino acid [Try$^{472}$ has been shown to be 1 of 4 tyrosines in PLC-γ that are phosphorylated by the EGF receptor tyrosine kinase (Wahl M. I., et al., *J. Biol. Chem.*, 1990;265:3944–3948), and the peptides derived from the enzyme sequence surrounding this site are excellent substrates for the enzyme], 10 µM ATP containing 1 µCi of [$^{32}$]ATP and incubated for 10 minutes at room temperature. The reaction was terminated by the addition of 2 mL of 75 mM phosphoric acid, and the contents of the reaction passed through a 2.5 cm phosphocellulose filter disc to bind the peptide. The filter was washed five times with 75 mM phosphoric acid, placed in a vial along with 5 mL of scintillation fluid (Ready gel, Beckman), and counted on a scintillation counter.

The compounds of Formula I have also exhibited good inhibitor activity against other cyclin-dependent kinase enzymes such as cdk2/cyclinE, cdk2/cyclinA, and cdk1/cyclinB.

When measured against cdk2/E, the invention compounds exhibited $IC_{50}$ values ranging generally from about 0.004 to greater than 5 µM. Against cdk2/A, the compounds exhibited $IC_{50}$ values ranging from about 0.028 to greater than 5 µM, and against cdk2/B, generally from about 0.214 to greater than 5 µM. The assays were carried out as described above, and specific data is given in Table 1 above.

Cdk5/p25 Proline-directed Protein Kinase Assay Protocol

Source of enzyme: recombinant baculovirus-infected insect cells sf9—expressed recombinant Cdk5-p25 complex Purpose: To evaluate the ability of test agents to inhibit Cdk5/p25 phosphorylation of Histone H1.

Method: Baculovirus-insect cell His-tagged Cdk5/Glu-tagged p25 (or GST-p25) enzyme complex is diluted to a concentration of 50 ng/20 µL in Enzyme Dilution Buffer (EDB—50 mM Tris-HCl [pH 8.0], 10 mM NaCl, 10 mM $MgCl_2$, and 1 mM DTT). A 20 µL sample of test agent (diluted in EDB) is then combined with 20 µL of the of the final Cdk5/p25 enzyme preparation and allowed to stand for 5 minutes at room temperature. Twenty-five microliters of substrate solution containing 115 µL/mL Histone H1, 30 µM ATP (vanadate-free), and 30 µCi/mL γ-$^{33}$P ATP (Amersham) in EDB is then added to the test agent/enzyme preparation and shaken at 30° C. for 45 minutes. A 50 µL sample of the final preparation is added to 100 mL of 150 mM phosphoric acid on ice for 30 minutes to facilitate precipitation. The precipitate is then filtered through a 96 well phosphocellucose filter plate and subsequently rinsed 3 times with 75 mM phosphoric acid. Each well then receives 20 µL of scintillation cocktail, and the plates are counted for beta emissions using a Trilux Counter ($^{33}$P filter protocol). Test samples are compared to Control (no test agent present; as 0% inhibition) and Baseline level (no enzyme, no test agent; as 100% inhibition) beta emissions to determine the percent inhibition of Histone H1 phosphorylation.

The invention compounds can be formulated in conventional manners to provide convenient dosage forms for delivery to mammals by various routes, including oral, parenteral (i.e., subcutaneous, intravenous, and intramuscular), transdermal, e.g. slow release skin patch or cream, as well as by slow release delivery devices such as osmotic pumps, suppositories, and buccal seals. The following examples further illustrate how the compounds are readily formulated.

| 50 mg Tablet Formulation | | |
|---|---|---|
| Per Tablet | | Per 10,000 Tablets |
| 0.050 g | Example 20 | 500 g |
| 0.080 g | Lactose | 800 g |
| 0.010 g | corn starch (for mix) | 100 g |
| 0.008 g | corn starch (for paste) | 80 g |
| 0.148 g | | 1480 g |
| 0.002 g | magnesium stearate (1%) | 20 g |
| 0.150 g | | 1500 g |

The quinazoline, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No. 16 screen. The mixture is lubricated with 1% magnesium stearate and compressed into tablets in a conventional tableting machine. The tablets are useful for treating cancers such as breast, prostate, lung, ovarian, colon, pancreatic, melanoma, esophageal, brain, Kaposi's sarcoma, and lymphomas, or neurodegenerative disorders such as Alzheimer's.

| Preparation of Oral Suspension | |
|---|---|
| Ingredient | Amount |
| Example 20 | 500 mg |
| Sorbitol solution (70% N.F.) | 40 mL |
| Sodium benzoate | 150 mg |
| Saccharin | 10 mg |
| Cherry flavor | 50 mg |
| Distilled water qs | 100 mL |

The sorbitol solution is added to 40 mL of distilled water, and the quinazoline is suspended therein. The saccharin, sodium benzoate, and flavoring are added and dissolved. The volume is adjusted to 100 mL with distilled water. Each milliliter of syrup contains 5 mg of invention compound.

Example 53

Preparation of Parenteral Solution

In a solution of 700 mL of propylene glycol and 200 mL of water for injection is suspended 20.0 g of Example 20 with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

Example 54

Suppositories

A mixture of 400 mg of Example 20, and 600 mg of theobroma oil is stirred at 60° C. to uniformity. The mixture is cooled and allowed to harden in a tapered mold to provide a 1 g suppository.

Example 55

Slow Release Formulation

Five hundred milligrams of Example 20 is converted to a hydrochloride salt and placed into an Oros osmotic pump for controlled release for treatment of atherosclerosis.

Example 56

Skin Patch Formulation

Fifty milligrams of Example 20 is admixed with 50 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

What is claimed is:

1. A compound of Formula I:

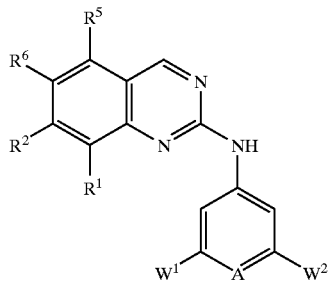

wherein,
$R^1$ is hydrogen, alkyl, alkyl substituted with at least one of amine, halogen, hydroxy, or alkoxy, cycloalkyl, or 4–10 membered heterocyclyl having 1–3 heteroatoms selected from O, S or N;
$R^2$ is OH, alkyloxy, aryloxy, or $NR^3R^4$;
A is N, or $CW^3$;
$R^3$ and $R^4$ are independently hydrogen, alkyl, alkenyl, alkynyl, $(CH_2)_nAr$, cycloalkyl, 4–10 membered heterocyclyl having 1–3 heteroatoms selected from O, S, or N, or a 4–9 membered heteroaryl having 1–4 heteroatoms selected from O, S or N, or $R^3$ and $R^4$ together with the nitrogen to which they are attached optionally may form a ring having 3 to 7 carbon atoms and said ring optionally contains 1, 2 or 3 heteroatoms selected from the group consisting of nitrogen, substituted nitrogen, oxygen and sulfur including S(O) and $S(O)_2$, said ring also may be additionally substituted with up to 3 groups selected from alkyl, haloalkyl, $NR^8C(O)R^9$, $C(O)OR^8$, $C(O)R^8$, $C(O)NR^8R^9$, $NR^8R^9$, $NR^8SO_2R^9$, $OR^8$, $SO_2NR^3R^4$, or $SR^8$;
$W^1$ and $W^2$ are independently selected from $NR^3R^4$, $N(O)R^3R^4$, $NR^3R^4X$, $OR^3$, $SR^3$, hydrogen, halogen, haloalkyl, $COR^3$, $CO_2R^3$, $CONR^3R^4$, $S(O)R^3$, $SO_2R^3$, $SO_2NR^3R^4$, $SO_3R^3$, $P(O)(OR^3)_2$, CHO, CN, nitro, alkyl, $T(CH_2)_mQR^8$, $C(O)T(CH_2)_mQR^8$, or $T(CH_2)_mCO_2R^8$ where m is 1–6, T is O, S, $NR^3$, $N(O)R^3$, $NR^3R^4X$, or $CR^3R^4$, and Q is O, S, $NR^9$, $N(O)R^9$ or $NR^9R^{10}X$, or $NR^9C(O)T(CH_2)_mQR^9$;
$R^5$ is hydrogen, or alkyl;
$R^6$ is hydrogen, alkyl, halogen, haloalkyl, alkynyl, alkenyl, $COR^3$, $CO_2R^3$, $CONR^3R^4$, $SO_2NR^3R^4$, $SO_2R^3$, $SO_3R^3$, $P(O)(OR^3)_2$, aldehyde, nitrile, nitro, $OR^3$, or $NR^3R^4$
$W^3$ is hydrogen, $NR^3R^4$, $N(O)R^3R^4$, $NR^3R^4R^8X$, OH, $OR^3$, SH, $SR^3$, halogen, $COR^3$, $CO_2R^3$, $CONR^3R^4$, $S(O)R^3$, $SO_2R^3$, $SO_2NR^3R^4$, $SO_3R^3$, $(CH_2)_nP(O)(OR^3)_2$, $NR^3SO_2R^4$, aldehyde, nitrile, nitro, alkyl, $T(CH_2)_m QR^8$, $C(O)T(CH_2)_mQR^8$, $NR^8C(O)T(CH_2)_mQR^{11}$, or $T(CH_2)_mCO_2R^3$ where m and n are independently 1–6, T is O, S, $NR^3$, $N(O)R^3$, or $CR^3R^4$, and Q is O, S, $NR^9$, $N(O)R^9$ or $NR^9R^{10}X$;
$R^8$, $R^9$, $R^{10}$ and $R^{11}$ are hydrogen, alkyl, or aryl;
X is a halogen;
or a pharmaceutically acceptable salt thereof.
2. A compound of claim 1 wherein $R^1$ is alkyl.
3. A compound of claim 1 wherein $R^1$ is isopropyl.
4. A compound of claim 1 wherein $R^1$ is cycloalkyl.
5. A compound of claim 1 wherein $R^1$ is cyclopentyl.
6. A compound of claim 1 wherein $R^2$ is hydroxy.
7. A compound of claim 1 wherein $R^2$ is alkyloxy.
8. A compound of claim 1 wherein $R^2$ is methoxy.
9. A compound of claim 1 wherein $R^2$ is $NR^3R^4$.
10. A compound of claim 1 wherein A is $CW^3$.
11. A compound of claim 1 wherein $W^3$ is piperidine.
12. A compound of claim 1 wherein $W^3$ is substituted piperidine.
13. A compound of claim 1 wherein $W^3$ is pyrrolidine.
14. A compound of claim 1 wherein $W^3$ is substituted pyrrolidine.
15. A compound of claim 1 wherein $W^3$ is piperazine.
16. A compound of claim 1 wherein $W^3$ is substituted piperazine.
17. A compound of claim 1 wherein $W^3$ is hydrogen.
18. A compound of claim 1 wherein $W^2$ and $W^3$ are hydrogen.
19. A compound of claim 1 wherein $R^5$ is hydrogen.
20. A compound of claim 1 wherein $R^5$ is alkyl.
21. A compound of claim 1 wherein $R^6$ is hydrogen.
22. A compound of claim 1 wherein $R^6$ is alkyl.
23. A compound of claim 1 wherein $W^1$, $W^2$, and $W^3$ are hydrogen.
24. A compound of claim 1 wherein $R^5$ and $R^6$ are hydrogen.
25. A compound of claim 1 wherein $W^1$, $W^2$, and $W^3$ are hydrogen, and $R^1$ is alkyl.
26. A compound of claim 1 wherein $W^1$, $W^2$, and $W^3$ are hydrogen, and $R^1$ is cycloalkyl.
27. A compound of claim 1 wherein $W^3$ is piperidine or substituted piperidine, and $R^1$ is alkyl or cycloalkyl.
28. A compound of claim 1 wherein $W^3$ is pyrrolidine or substituted pyrrolidine, and $R^1$ is alkyl or cycloalkyl.
29. A compound of claim 1 wherein $W^3$ is piperazine or substituted piperazine, and $R^1$ is alkyl or cycloalkyl.
30. A compound of claim 1 wherein $W^3$ is piperidine or substituted piperidine, $R^2$ is alkyloxy, and $R^1$ is alkyl or cycloalkyl.

31. A compound of claim 1 wherein W³ is pyrrolidine or substituted pyrrolidine, R² is alkyloxy, and R¹ is alkyl or cycloalkyl.

32. A compound of claim 1 wherein W³ is piperazine or substituted piperazine, R² is alkyloxy, and R¹ is alkyl or cycloalkyl.

33. A compound selected from:
(8-Isopropyl-7-methoxy-quinazolin-2-yl)-phenyl-amine;
(8-Cyclopentyl-7-methoxy-quinazolin-2-yl)-phenyl-amine;
(8-Isopropyl-7-methoxy-quinazolin-2-yl)-(4-piperidin-1-yl-phenyl)-amine;
(8-Isopropyl-7-methoxy-quinazolin-2-yl)-(4-pyrrolidin-1-yl-phenyl)-amine;
(8-Cyclopentyl-7-methoxy-quinazolin-2-yl)-(4-piperidin-1-yl-phenyl)-amine;
(8-Cyclopentyl-7-methoxy-quinazolin-2-yl)-(4-pyrrolidin-1-yl-phenyl)-amine;
8-Isopropyl-2-phenylamino-quinazolin-7-ol;
4-[4-(8-Isopropyl-7-methoxy-quinazolin-2-ylamino)-phenyl]-piperazine-1-carboxylic acid tert-butyl ester;
4-[4-(8-Cyclopentyl-7-methoxy-quinazolin-2-ylamino)-phenyl]-piperazine-1-carboxylic acid tert-butyl ester;
(8-Cyclopentyl-7-methoxy-quinazolin-2-yl)-(4-piperazin-1-yl-phenyl)-amine;
8-Cyclopentyl-2-(4-piperazin-1-yl-phenylamino)-quinazolin-7-ol;
2-Amino-1-{4-[4-(8-cyclopentyl-7-methoxy-quinazolin-2-ylamino)-phenyl]-piperazin-1-yl}-ethanone;
8-Isopropyl-2-(4-piperazin-1-yl-phenylamino)-quinazolin-7-ol;
(8-Isopropyl-7-methoxy-quinazolin-2-yl)-(4-piperazin-1-yl-phenyl)-amine;
2-Amino-1-{4-[4-(8-cyclopentyl-7-hydroxy-quinazolin-2-ylamino)-phenyl]-piperazin-1-yl}-ethanone;
2-Amino-1-{4-[4-(8-isopropyl-7-methoxy-quinazolin-2-ylamino)-phenyl]-piperazin-1-yl}-ethanone;
2-Amino-1-{4-[4-(7-hydroxy-8-isopropyl-quinazolin-2-ylamino)-phenyl]-piperazin-1-yl}-ethanone;
2-Amino-1-{4-[4-(8-cyclopentyl-7-methoxy-quinazolin-2-ylamino)-phenyl]-piperazin-1-yl}-4-methyl-pentan-1-one;
2-Amino-1-{4-[4-(8-cyclopentyl-7-hydroxy-quinazolin-2-ylamino)-phenyl]-piperazin-1-yl}-4-methyl-pentan-1-one;
2-Amino-1-{4-[4-(8-isopropyl-7-methoxy-quinazolin-2-ylamino)-phenyl]-piperazin-1-yl}-4-methyl-pentan-1-one;
2-Amino-1-{4-[4-(7-hydroxy-8-isopropyl-quinazolin-2-ylamino)-phenyl]-piperazin-1-yl}-4-methyl-pentan-1-one;
N-(4-{4-[4-(8-cyclopentyl-7-methoxy-quinazolin-2-ylamino)-phenyl]-piperazin-1-yl}-4-oxo-butyl)-acetamide;
N-(4-{4-[4-(8-Cyclopentyl-7-hydroxy-quinazolin-2-ylamino)-phenyl]-piperazin-1-yl}-4-oxo-butyl)-acetamide;
N-(4-{4-[4-(8-isopropyl-7-methoxy-quinazolin-2-ylamino)-phenyl]-piperazin-1-yl}-4-oxo-butyl)-acetamide;
N-(4-{4-[4-(7-Hydroxy-8-isopropyl-quinazolin-2-ylamino)-phenyl]-piperazin-1-yl}-4-oxo-butyl)-acetamide;
8-Isopropyl-2-(pyridin-4-ylamino)-quinazolin-7-ol;
(8-Isopropyl-7-methoxy-quinazolin-2-yl)-pyridin-4-yl-amine;
(8-cyclopentyl-7-methoxy-quinazolin-2-yl)-pyridin-4-yl-amine;
8-cyclopentyl-2-(pyridin-4-ylamino)-quinazolin-7-ol;
(8-Cyclopentyl-7-methoxy-quinazolin-2-yl)-[4-(5-methyl-hexahydro-pyrrolo[3,4-c]pyrrol-2-yl)-phenyl]-amine;
8-Cyclopentyl-2-[4-(5-methyl-hexahydro-pyrrolo[3,4-c]pyrrol-2-yl)-phenylamino]-quinazolin-7-ol;
(8-Isopropyl-7-methoxy-quinazolin-2-yl)-[4-(5-methyl-hexahydro-pyrrolo[3,4-c]pyrrol-2-yl)-phenyl]-amine;
8-Isopropyl-2-[4-(5-methyl-hexahydro-pyrrolo[3,4-c]pyrrol-2-yl)-phenylamino]-quinazolin-7-ol;
[4-(3-Amino-pyrrolidin-1-yl)-phenyl]-(8-cyclopentyl-7-methoxy-quinazolin-2-yl)-amine;
2-[4-(3-Amino-pyrrolidin-1-yl)-phenylamino]-8-cyclopentyl-quinazolin-7-ol;
[4-(3-Amino-pyrrolidin-1-yl)-phenyl]-(8-isopropyl-7-methoxy-quinazolin-2-yl)-amine;
2-[4-(3-Amino-pyrrolidin-1-yl)-phenylamino]-8-isopropyl-quinazolin-7-ol;
N-{1-[4-(8-Cyclopentyl-7-methoxy-quinazolin-2-ylamino)-phenyl]-pyrrolidin-3-yl}-acetamide;
N-{1-[4-(8-Cyclopentyl-7-hydroxy-quinazolin-2-ylamino)-phenyl]-pyrrolidin-3-yl}-acetamide;
N-{1-[4-(8-Isopropyl-7-methoxy-quinazolin-2-ylamino)-phenyl]-pyrrolidin-3-yl}-acetamide;
N-{1-[4-(8-Isopropyl-7-hydroxy-quinazolin-2-ylamino)-phenyl]-pyrrolidin-3-yl}-acetamide;
1-{4-[4-(8-Isopropyl-7-methoxy-quinazolin-2-ylamino)-phenyl]-piperazin-1-yl}-ethanone;
1-{4-[4-(7-Hydroxy-8-isopropyl-quinazolin-2-ylamino)-phenyl]-piperazin-1-yl}-ethanone;
{4-[4-(8-Cyclopentyl-7-methoxy-quinazolin-2-ylamino)-phenyl]-piperazin-1-yl}-pyrrolidin-2-yl-methanone;
{4-[4-(8-Cyclopentyl-7-Hydroxy-quinazolin-2-ylamino)-phenyl]-piperazin-1-yl}-pyrrolidin-2-yl-methanone;
1-{4-[4-(8-Cyclopentyl-7-methoxy-quinazolin-2-ylamino)-phenyl]-piperazin-1-yl}-ethanone;
1-{4-[4-(8-Cyclopentyl-7-hydroxy-quinazolin-2-ylamino)-phenyl]-piperazin-1-yl}-ethanone;
{4-[4-(8-Isopropyl-7-methoxy-quinazolin-2-ylamino)-phenyl]-piperazin-1-yl}-pyrrolidin-2-yl-methanone;
{4-[4-(7-Hydroxy-8-isopropyl-quinazolin-2-ylamino)-phenyl]-piperazin-1-yl}-pyrrolidin-2-yl-methanone;
2-Amino-1-{4-[4-(8-isopropyl-quinazolin-2-ylamino)-phenyl]-piperazin-1-yl}-propan-1-one;
2-Amino-1-{4-[4-(7-hydroxy-8-isopropyl-quinazolin-2-ylamino)-phenyl]-piperazin-1-yl}-propan-1-one;
2-Amino-1-{4-[4-(8-cyclopentyl-7-methoxy-quinazolin-2-ylamino)-phenyl]-piperazin-1-yl}-propan-1-one;
2-Amino-1-{4-[4-(8-cyclopentyl-7-hydroxy-quinazolin-2-ylamino)-phenyl]-piperazin-1-yl}-propan-1-one;
1-{4-[4-(8-Cyclopentyl-7-methoxy-quinazolin-2-ylamino)-phenyl]-piperazin-1-yl}-propan-1-one;
1-{4-[4-(8-Cyclopentyl-7-hydroxy-quinazolin-2-ylamino)-phenyl]-piperazin-1-yl}-propan-1-one;
1-{4-[4-(8-Isopropyl-7-methoxy-quinazolin-2-ylamino)-phenyl]-piperazin-1-yl}-propan-1-one;
1-{4-[4-(7-Hydroxy-8-isopropyl-quinazolin-2-ylamino)-phenyl]-piperazin-1-yl}-propan-1-one;
2-Amino-1-{4-[4-(8-cyclopentyl-7-hydroxy-5,6-dihydro-quinazolin-2-ylamino)-phenyl]-piperazin-1-yl}-ethanone;
2-Amino-1-{4-[4-(8-cyclopentyl-7-methoxy-5,6-dihydro-quinazolin-2-ylamino)-phenyl]-piperazin-1-yl}-ethanone;

2-Amino-1-{4-[4-(8-cyclopentyl-7-hydroxy-5,8-dihydro-quinazolin-2-ylamino)-phenyl]-piperazin-1-yl}-ethanone;
2-Amino-1-{4-[4-(8-cyclopentyl-7-methoxy-5,8-dihydro-quinazolin-2-ylamino)-phenyl]-piperazin-1-yl}-ethanone;
(4-Fluoro-3-methyl-phenyl)-(8-isopropyl-7-methoxy-quinazolin-2-yl)-amine;
2-(4-Fluoro-3-methyl-phenylamino)-8-isopropyl-quinazolin-7-ol;
(8-Cyclopentyl-7-methoxy-quinazolin-2-yl)-(4-fluoro-3-methyl-phenyl)-amine;
8-Cyclopentyl-2-(4-fluoro-3-methyl-phenylamino)-quinazolin-7-ol;
(3-Chloro-4-fluoro-phenyl)-(8-isopropyl-7-methoxy-quinazolin-2-yl)-amine;
2-(3-Chloro-4-fluoro-phenylamino)-8-isopropyl-quinazolin-7-ol;
(3-Chloro-4-fluoro-phenyl)-(8-cyclopentyl-7-methoxy-quinazolin-2-yl)-amine;
2-(3-Chloro-4-fluoro-phenylamino)-8-cyclopentyl-quinazolin-7-ol;
(3,4-Difluoro-phenyl)-(8-isopropyl-7-methoxy-quinazolin-2-yl)-amine;
2-(3,4-Difluor-phenylamino)-8-isopropyl-quinazolin-7-ol;
(8-Cyclopentyl-7-methoxy-quinazolin-2-yl)-(3,4-difluoro-phenyl)-amine;
8-Cyclopentyl-2-(3,4-difluoro-phenylamino)-quinazolin-7-ol;
(3-Fluoro-4-piperazin-1-yl-phenyl)-(8-isopropyl-7-methoxy-quinazolin-2-yl)-amine;
2-(3-Fluoro-4-piperazin-1-yl-phenylamino)-8-isopropyl-quinazolin-7-ol;
(8-Cyclopentyl-7-methoxy-quinazolin-2-yl)-(3-fluoro-4-piperazin-1-yl-phenyl)-amine;
8-Cyclopentyl-2-(3-fluoro-4-piperazin-1-yl-phenylamino)-quinazolin-7-ol;
[4-(3-Amino-pyrrolidin-1-yl)-3-fluoro-phenyl]-(8-isopropyl-7-methoxy-quinazolin-2-yl)-amine;
2-[4-(3-Amino-pyrrolidin-1-yl)-3-fluoro-phenylamino]-8-isopropyl-quinazolin-7-ol;
[4-(3-Amino-pyrrolidin-1-yl)-3-fluoro-phenyl]-(8-cyclopentyl-7-methoxy-quinazolin-2-yl)-amine;
2-[4-(3-Amino-pyrrolidin-1-yl)-3-fluoro-phenylamino]-8-cyclopentyl-quinazolin-7-ol;
(8-Isopropyl-7-methoxy-quinazolin-2-yl)-{4-[4-(3-piperazin-1-yl-propyl)-piperidin-1-yl]-phenyl}-amine;
8-Isopropyl-2-{4-[4-(3-piperazin-1-yl-propyl)-piperidin-1-yl]-phenylamino}-quinazolin-7-ol;
(8-Cyclopentyl-7-methoxy-quinazolin-2-yl)-{4-[4-(3-piperazin-1-yl-propyl)-piperidin-1-yl]-phenyl}-amine;
8-Cyclopentyl-2-{4-[4-(3-piperazin-1-yl-propyl)-piperidin-1-yl]-phenylamino}-quinazolin-7-ol;
{3-Chloro-4-[4-(3-piperazin-1-yl-propyl)-piperidin-1-yl]-phenyl}-(8-isopropyl-7-methoxy-quinazolin-2-yl)-amine;
2-{3-Chloro-4-[4-(3-piperazin-1-yl-propyl)-piperidin-1-yl]-phenylamino}-8-isopropyl-quinazolin-7-ol;
{3-Chloro-4-[4-(3-piperazin-1-yl-propyl)-piperidin-1-yl]-phenyl}-(8-cyclopentyl-7-methoxy-quinazolin-2-yl)-amine;
2-{3-Chloro-4-[4-(3-piperazin-1-yl-propyl)-piperidin-1-yl]-phenylamino}-8-cyclopentyl-quinazolin-7-ol;
(4-{4-[3-(3-Amino-pyrrolidin-1-yl)-propyl]-piperidin-1-yl}-3-chloro-phenyl)-(8-isopropyl-7-methoxy-quinazolin-2-yl)-amine;
2-(4-{4-[3-(3-Amino-pyrrolidin-1-yl)-propyl]-piperidin-1-yl}-3-chloro-phenylamino)-8-isopropyl-quinazolin-7-ol;
(4-{4-[3-(3-Amino-pyrrolidin-1-yl)-propyl]-piperidin-1-yl}-3-chloro-phenyl)-(8-cyclopentyl-7-methoxy-quinazolin-2-yl)-amine;
2-(4-{4-[3-(3-Amino-pyrrolidin-1-yl)-propyl]-piperidin-1-yl}-3-chloro-phenylamino)-8-cyclopentyl-quinazolin-7-ol;
(4-{4-[3-(3-Amino-pyrrolidin-1-yl)-propyl]-piperidin-1-yl}-phenyl)-(8-isopropyl-7-methoxy-quinazolin-2-yl)-amine;
2-(4-{4-[3-(3-Amino-pyrrolidin-1-yl)-propyl]-piperidin-1-yl}-phenylamino)-8-isopropyl-quinazolin-7-ol;
(4-{4-[3-(3-Amino-pyrrolidin-1-yl)-propyl]-piperidin-1-yl}-phenyl)-(8-cyclopentyl-7-methoxy-quinazolin-2-yl)-amine;
2-(4-{4-[3-(3-Amino-pyrrolidin-1-yl)-propyl]-piperidin-1-yl}-phenylamino)-8-cyclopentyl-quinazolin-7-ol;
(8-Isopropyl-7-methoxy-quinazolin-2-yl)-{4-[4-(4-methoxy-phenyl)-piperazin-1-yl]-phenyl}-amine;
8-Isopropyl-2-{4-[4-(4-methoxy-phenyl)-piperazin-1-yl]-phenylamino}-quinazolin-7-ol;
(8-Cyclopentyl-7-methoxy-quinazolin-2-yl)-{4-[4-(4-methoxy-phenyl)-piperazin-1-yl]-phenyl}-amine;
8-Cyclopentyl-2-{4-[4-(4-methoxy-phenyl)-piperazin-1-yl]-phenylamino}-quinazolin-7-ol;
(8-Isopropyl-7-methoxy-quinazolin-2-yl)-[4-(3,3,4-trimethyl-piperazin-1-yl)-phenyl]-amine;
8-Isopropyl-2-[4-(5-methyl-hexahydro-pyrrolo[3,4-c]pyrrol-2-yl)-phenylamino]-quinazolin-7-ol;
(8-Cyclopentyl-7-methoxy-quinazolin-2-yl)-[4-(5-methyl-hexahydro-pyrrolo[3,4-c]pyrrol-2-yl)-phenyl]-amine;
8-Cyclopentyl-2-[4-(5-methyl-hexahydro-pyrrolo[3,4-c]pyrrol-2-yl)-phenylamino]-quinazolin-7-ol;
8-Isopropyl-2-[4-(3,3,4-trimethyl-piperazin-1-yl)-phenylamino]-quinazolin-7-ol;
(8-Cyclopentyl-7-methoxy-quinazolin-2-yl)-[4-(3,3,4-trimethyl-piperazin-1-yl)-phenyl]-amine;
8-Cyclopentyl-2-[4-(3,3,4-trimethyl-piperazin-1-yl)-phenylamino]-quinazolin-7-ol;
(8-Isopropyl-7-methoxy-quinazolin-2-yl)-[4-(5-methyl-hexahydro-pyrrolo[3,4-c]pyrrol-2-yl)-phenyl]-amine;
(8-Cyclopentyl-7-methoxy-quinazolin-2-yl)-(4-perhydro-1,4-diazepin-1-yl-phenyl)-amine;
8-Cyclopentyl-2-(4-perhydro-1,4-diazepin-1-yl-phenylamino)-quinazolin-7-ol;
2-{4-[4-(8-Cyclopentyl-7-methoxy-quinazolin-2-ylamino)-phenyl]-2,6-dimethyl-piperazin-1-yl}-ethanol;
(8-Cyclopentyl-7-methoxy-quinazolin-2-yl)-[4-(2-methylamino-ethoxy)-phenyl]-amine;
1-{4-[4-(8-Cyclopentyl-7-methoxy-quinazolin-2-ylamino)-phenyl]-perhydro-1,4-diazepin-1-yl}-ethanone;
8-Cyclopentyl-2-[4-(3,3-dimethyl-piperazin-1-yl)-phenylamino]-quinazolin-7-ol;
(8-Cyclopentyl-7-methoxy-quinazolin-2-yl)-[4-(3,3-dimethyl-piperazin-1-yl)-phenyl]-amine;
1-{4-[4-(8-Cyclopentyl-7-hydroxy-quinazolin-2-ylamino)-phenyl]-perhydro-1,4-diazepin-1-yl}-ethanone;
1-{4-[4-(7-Amino-8-cyclopentyl-quinazolin-2-ylamino)-phenyl]-piperazin-1-yl}-ethanone;
1-{4-[4-(8-Cyclopentyl-7-methylamino-quinazolin-2-ylamino)-phenyl]-piperazin-1-yl}-ethanone;

1-{4-[4-(8-Cyclopentyl-7-dimethylamino-quinazolin-2-ylamino)-phenyl]-piperazin-1-yl}-ethanone;
(8-Cyclopentyl-7-methoxy-5-methyl-quinazolin-2-yl)-(4-perhydro-1,4-diazepin-1-yl-phenyl)-amine;
8-Cyclopentyl-5-methyl-2-(4-perhydro-1,4-diazepin-1-yl-phenylamino)-quinazolin-7-ol;
2-{4-[4-(8-Cyclopentyl-7-methoxy-5-methyl-quinazolin-2-ylamino)-phenyl]-2,6-dimethyl-piperazin-1-yl}-ethanol;
(8-Cyclopentyl-7-methoxy-5-methyl-quinazolin-2-yl)-[4-(2-methylamino-ethoxy)-phenyl] -amine;
1-{4-[4-(8-Cyclopentyl-7-methoxy-5-methyl-quinazolin-2-ylamino)-phenyl] -perhydro-1,4-diazepin-1-yl}-ethanone;
8-Cyclopentyl-2-[4-(3,3-dimethyl-piperazin-1-yl)-phenylamino]-5-methyl-quinazolin-7-ol;
(8-Cyclopentyl-7-methoxy-5-methyl-quinazolin-2-yl)-[4-(3,3-dimethyl-piperazin-1-yl)-phenyl]-amine;
1-{4-[4-(8-Cyclopentyl-7-hydroxy-5-methyl-quinazolin-2-ylamino)-phenyl] -perhydro-1,4-diazepin-1-yl}-ethanone;
1-{4-[4-(8-Cyclopentyl-7-hydroxy-5-methyl-quinazolin-2-ylamino)-phenyl] -piperazin-1-yl}-ethanone;
1-{4-[4-(8-Cyclopentyl-7-methoxy-5-methyl-quinazolin-2-ylamino)-phenyl] -piperazin-1-yl}-ethanone;
8-Cyclopentyl-5-methyl-2-(4-piperazin-1-yl-phenylamino)-quinazolin-7-ol;
(8-Cyclopentyl-7-methoxy-5-methyl-quinazolin-2-yl)-(4-piperazin-1-yl-phenyl)-amine;
(8-Cyclopentyl-7-methoxy-5-methyl-quinazolin-2-yl)-{4-[4-(3-piperazin-1-yl-propyl)-piperidin-1-yl]-phenyl}-amine;
8-Cyclopentyl-5-methyl-2-{4-[4-(3-piperazin-1-yl-propyl)-piperidin-1-yl] -phenylamino}-quinazolin-7-ol.

34. A compound of Formula II:

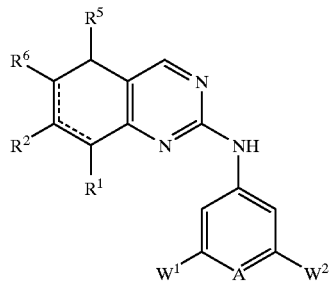

wherein,
the dotted line represents a bond at the $C_5-C_6$, $C_6-C_7$, or $C_7-C_8$ position,
$R^1$ is hydrogen, alkyl, alkyl substituted with at least one of amine, halogen, hydroxy, or alkoxy, cycloalkyl, or 4–10 membered heterocyclyl having 1–3 heteroatoms selected from O, S or N;
A is N, or $CW^3$;
$R^3$ and $R^4$ are independently hydrogen, alkyl, alkenyl, alkynyl, $(CH_2)_n Ar$, cycloalkyl, 4–10 membered heterocyclyl having 1–3 heteroatoms selected from O, S or N, or a 4–9 membered heteroaryl having 1–4 heteroatoms selected from O, S or N, or $R^3$ and $R^4$ together with the nitrogen to which they are attached optionally may form a ring having 3 to 7 carbon atoms and said ring optionally contains 1, 2 or 3 heteroatoms selected from the group consisting of nitrogen, substituted nitrogen, oxygen and sulfur including S(O) and S(O)$_2$ said ring also may be additionally substituted with up to 3 groups selected from alkyl, haloalkyl, $NR^8C(O)R^9$, $C(O)OR^8$, $C(O)R^8$, $C(O)NR^8R^9$, $NR^8R^9$, $NR^8SO_2R^9$, $OR^8$, $SO_2NR^3R^4$, or $SR^8$;
$W^1$ and $W^2$ are independently selected from $NR^3R^4$, $N(O)R^3R^4$, $NR^3R^4X$, $OR^3$, $SR^3$, hydrogen, halogen, haloalkyl, $COR^3$, $CO_2R^3$, $CONR^3R^4$, $S(O)R^3$, $SO_2R^3$, $SO_2NR^3R^4$, $SO_3R^3$, $P(O)(OR^3)_2$, aldehyde, nitrile, nitro, alkyl, $T(CH_2)_m QR^8$, $C(O)T(CH_2)_m QR^8$, or $T(CH^2)_m CO_2R^8$ where m is 1–6, T is O, S, $NR^3$, $N(O)R^3_9$, $NR^3R^4X$, or $CR^3R^4$, and Q is O, S, $NR^9$, $N(O)R^9$ or $NR^9R^{10}X$, or $NR^9C(O)T(CH_2)_m QR^9$;
$R^5$ is hydrogen, or alkyl;
$R^6$ is hydrogen, alkyl, halogen, haloalkyl, alkynyl, alkenyl, $COR^3$, $CO_2R^3$, $CONR^3R^4$, $SO_2NR^3R^4$, $SO_2R^3$, $SO_3R^3$, $P(O)(OR^3)_2$, CHO, CN, nitro, $OR^3$, or $NR^3R^4$
$W^3$ is hydrogen, $NR^3R^4$, $N(O)R^3R^4$, $NR^3R^4R^8X$, OH, $OR^3$, SH, $SR^3$, halo, $COR^3$, $CO_2R^3$, $CONR^3R^4$, $S(O)R^3$, $SO_2R^3$, $SO_2NR^3R^4$, $SO_3R^3$, $(CH_2)_n P(O)(OR^3)_2$, $NR^3SO_2R^4$, aldehyde, nitrile, nitro, alkyl, $T(CH_2)_m QR^8$, $C(O)T(CH_2)_m QR^8$, $NR^8C(O)T(CH_2)_m QR^{11}$, or $T(CH^2)_m CO_2R^3$ where n and m independently are 1–6, T is O, S, $NR^3$, $N(O)R^3$, or $CR^3R^4$; and Q is O, S, $NR^9$, $N(O)R^9$ or $NR^9R^{10}X$;
$R^8$, $R^9$, $R^{10}$ and $R^{11}$ are hydrogen, alkyl, or aryl;
X is a halogen;
or a pharmaceutically acceptable salt thereof.

35. The compound of claim 34, wherein $R^1$ is alkyl.
36. The compound of claim 34, wherein $R^1$ is isopropyl.
37. The compound of claim 34, wherein $R^1$ is cycloalkyl.
38. The compound of claim 34, wherein $R^1$ is cyclopentyl.
39. The compound of claim 34, wherein $R^2$ is hydroxy.
40. The compound of claim 34, wherein $R^2$ is alkyloxy.
41. The compound of claim 34, wherein $R^2$ is methoxy.
42. The compound of claim 34, wherein $R^2$ is $NR^3R^4$.
43. The compound of claim 34, wherein A is $CW^3$.
44. The compound of claim 34, wherein $W^3$ is piperidine.
45. The compound of claim 34, wherein $W^3$ is substituted piperidine.
46. The compound of claim 34, wherein $W^3$ is pyrrolidine.
47. The compound of claim 34, wherein $W^3$ is substituted pyrrolidine.
48. The compound of claim 34, wherein $W^3$ is piperazine.
49. The compound of claim 34, wherein $W^3$ is substituted piperazine.
50. The compound of claim 34, wherein $W^3$ is hydrogen.
51. The compound of claim 34, wherein $W^2$ and $W^3$ are hydrogen.
52. The compound of claim 34, wherein $R^5$ is hydrogen.
53. The compound of claim 34, wherein $R^5$ is alkyl.
54. The compound of claim 34, wherein $R^6$ is hydrogen.
55. The compound of claim 34, wherein $R^6$ is alkyl.
56. The compound of claim 34, wherein $W^1$, $W^2$, and $W^3$ are hydrogen.
57. The compound of claim 34, wherein $R^5$ and $R^6$ are hydrogen.
58. The compound of claim 34, wherein $W^1$, $W^2$, and $W^3$ are hydrogen, and $R^1$ is alkyl.
59. The compound of claim 34, wherein $W^1$, $W^2$, and $W^3$ are hydrogen, and $R^1$ is cycloalkyl.
60. The compound of claim 34, wherein $W^3$ is piperidine or substituted piperidine, and $R^1$ is alkyl or cycloalkyl.
61. The compound of claim 34, wherein $W^3$ is pyrrolidine or substituted pyrrolidine, and $R^1$ is alkyl or cycloalkyl.

62. The compound of claim 34, wherein $W^3$ is piperazine or substituted piperazine, and $R^1$ is alkyl or cycloalkyl.

63. The compound of claim 34, wherein $W^3$ is piperidine or substituted piperidine, $R^2$ is alkyloxy, and $R^1$ is alkyl or cycloalkyl.

64. The compound of claim 34, wherein $W^3$ is pyrrolidine or substituted pyrrolidine, $R^2$ is alkyloxy, and $R^1$ is alkyl or cycloalkyl.

65. The compound of claim 34, wherein $W^3$ is piperazine or substituted piperazine, $R^2$ is alkyloxy, and $R^1$ is alkyl or cycloalkyl.

66. A pharmaceutical formulation comprising a compound of claim 1 in combination with a pharmaceutically acceptable carrier, diluent, or excipient.

* * * * *